US012642807B2

(12) United States Patent (10) Patent No.: US 12,642,807 B2
Richter Dayan (45) Date of Patent: Jun. 2, 2026

(54) METHODS AND COMPOSITIONS FOR TREATING AND PREVENTING SKIN BARRIER DISRUPTIONS

(71) Applicant: DERMAFENCE LTD, Jerusalem (IL)

(72) Inventor: Shulamit Richter Dayan, Jerusalem (IL)

(73) Assignee: DERMAFENCE LTD, Jerusalem (IL)

( * ) Notice: Subject to any disclaimer, the term of this patent is extended or adjusted under 35 U.S.C. 154(b) by 0 days.

(21) Appl. No.: 16/963,527

(22) PCT Filed: Feb. 4, 2019

(86) PCT No.: PCT/IL2019/050132
§ 371 (c)(1),
(2) Date: Jul. 21, 2020

(87) PCT Pub. No.: WO2019/150375
PCT Pub. Date: Aug. 8, 2019

(65) Prior Publication Data
US 2021/0046098 A1 Feb. 18, 2021

Related U.S. Application Data

(60) Provisional application No. 62/626,164, filed on Feb. 5, 2018.

(51) Int. Cl.
*A61K 31/685* (2006.01)
*A61K 8/31* (2006.01)
(Continued)

(52) U.S. Cl.
CPC .............. *A61K 31/685* (2013.01); *A61K 8/31* (2013.01); *A61K 8/36* (2013.01); *A61K 8/58* (2013.01);
(Continued)

(58) Field of Classification Search
CPC .... A61K 9/122; A61K 8/046; A61K 2300/00; A61K 9/0014; A61K 8/4993; A61K 8/86; A61K 47/34; A61K 47/14; A61K 9/1075; A61K 45/06; A61K 47/26; A61K 47/44; A61K 31/22; A61K 31/455; A61K 47/06; A61K 47/10; A61K 47/32; A61K 8/31; A61K 8/342; A61K 8/37; A61K 9/0031; A61K 9/0034; A61K 9/0043; A61K 9/0046; A61K 31/7056; A61K 47/36; A61K 47/38; A61K 8/361; A61K 8/362; A61K 31/522; A61K 47/12; A61K 8/731; A61K 8/87; A61K 9/107; A61K 9/124; A61K 2800/24; A61K 2800/242; A61K 2800/244; A61K 2800/30; A61K 31/20; A61K 31/265; A61K 31/355; A61K 31/59; A61K 31/65; A61K 38/13; A61K 38/28; A61K 38/31; A61K 47/18; A61K 47/24; A61K 8/34; A61K 8/345; A61K 8/42; A61K 8/736; A61K 8/8152; A61K 8/8158; A61K 8/922; A61K 9/0019; A61K 9/12; A61K 2800/31; A61K 31/167; A61K 31/19; A61K 31/201; A61K 31/341; A61K 31/375; A61K 31/56; A61K 31/573; A61K 31/593; A61K 33/34; A61K 36/00; A61K 9/0048; A61K 9/0053; A61K 9/0056; A61K 9/006; A61K 9/1273; A61K 9/20; A61K 2800/21; A61K 31/12; A61K 31/132; A61K 31/196; A61K 31/216; A61K 31/337; A61K 31/505; A61K 31/506; A61K 31/60; A61K 31/704; A61K 33/04; A61K 33/26; A61K 33/30; A61K 33/40; A61K 35/12; A61K 38/00; A61K 38/44; A61K 38/443; A61K 39/39591; A61K 47/02; A61K 47/183; A61K 47/22; A61K 47/46; A61K 47/6915; A61K 8/06; A61K 8/062; A61K 8/068; A61K 8/375; A61K 8/38; A61K 8/39; A61K 8/44; A61K 8/442; A61K 8/498; A61K 8/602; A61K 8/73; A61K 8/737; A61K 8/8141; A61K 8/8147; A61K 8/90; A61K 9/0009; A61K 9/0024; A61K 9/06; A61K 9/08; A61K 9/113; A61K 9/1274; A61K 9/5052; A61K 8/0295; A61K 2800/5426; A61K 8/064; A61K 8/463; A61K 8/817; A61K 8/8182; A61K 8/8194; A61K 8/894; A61K 8/671; A61K 8/891; A61K 31/203; A61K 31/23;
(Continued)

(56) References Cited

U.S. PATENT DOCUMENTS

2010/0305215 A1* 12/2010 Yamaguchi .............. A61K 8/86
514/738

FOREIGN PATENT DOCUMENTS

CN 104983599 A * 10/2015
JP 2006118245 A1 11/2006
(Continued)

OTHER PUBLICATIONS

JP2010229117A translation. (Year: 2010).*
(Continued)

*Primary Examiner* — Audrea B Coniglio
(74) *Attorney, Agent, or Firm* — FISHERBROYLES, LLP; Roger L. Browdy

(57) ABSTRACT

The present invention provides compositions and methods for treating, or attenuating and/or preventing skin barrier disruptions, skin insults and skin conditions in a subject. The lyotropic liquid crystal composition of the invention comprises at least one of phase changing material, and at least one stratum corneum component.

21 Claims, 11 Drawing Sheets

(51) Int. Cl.

| | |
|---|---|
| *A61K 8/36* | (2006.01) |
| *A61K 8/58* | (2006.01) |
| *A61K 8/92* | (2006.01) |
| *A61K 47/06* | (2006.01) |
| *A61K 47/12* | (2006.01) |
| *A61K 47/44* | (2017.01) |
| *A61P 17/02* | (2006.01) |
| *A61Q 19/00* | (2006.01) |

(52) U.S. Cl.

CPC ................ *A61K 8/92* (2013.01); *A61K 47/06* (2013.01); *A61K 47/12* (2013.01); *A61K 47/44* (2013.01); *A61P 17/02* (2018.01); *A61Q 19/00* (2013.01)

(58) Field of Classification Search

CPC ........ A61K 47/08; A61K 8/0216; A61K 8/27; A61K 8/585; A61K 8/88; A61K 8/893; A61K 8/898; A61K 8/899; A61K 2800/412; A61K 2800/43; A61K 2800/52; A61K 31/685; A61K 38/10; A61K 38/1825; A61K 8/11; A61K 8/19; A61K 8/347; A61K 8/36; A61K 8/58; A61K 8/92; A61K 9/0004; A61K 31/44; A61K 31/451; A61K 31/785; A61K 36/48; A61K 36/537; A61K 38/1808; A61K 38/1841; A61K 38/1858; A61K 38/1866; A61K 38/38; A61K 41/0042; A61K 41/0052; A61K 8/02; A61K 8/30; A61K 8/4933; A61K 8/60; A61K 8/68; A61K 8/892; A61K 8/988; A61K 9/0002; A61K 9/0021; A61K 9/7015; A61K 8/35; A61K 8/895; A61K 8/0291; A61K 8/675; A61K 8/732; A61K 8/04; A61K 8/676; A61K 8/0241; A61K 8/25; A61K 8/4973; A61K 8/8111; A61K 8/89; A61K 8/29; A61K 8/925; A61K 2800/592; A61K 8/14; A61K 8/416; A61K 8/4926; A61K 8/553; A61K 8/965; A61K 2800/413; A61K 31/415; A61K 31/4174; A61K 31/485; A61K 31/5517; A61K 8/0208; A61K 8/365; A61K 8/4946; A61K 8/66; A61K 9/5153; A61K 9/7061; A61K 31/554; A61K 2039/54; A61K 2039/55511; A61K 2039/55527; A61K 2039/55544; A61K 2039/55555; A61K 2039/55566; A61K 2800/59; A61K 2800/596; A61K 2800/884; A61K 31/55; A61K 39/39; A61K 49/0006; A61K 8/18; A61K 8/33; A61K 8/604; A61K 8/645; A61K 8/8176; A61K 9/10; A61K 9/127; A61K 9/1676; A61K 9/5146; A61K 9/7023; A61K 9/7038; A61Q 19/00; A61Q 5/00; A61Q 19/04; A61Q 19/08; A61Q 5/06; A61Q 5/12; A61Q 17/04; A61Q 19/10; A61Q 7/00; A61Q 19/02; A61Q 5/02; A61Q 17/00; A61Q 5/10; A61Q 19/007; A61Q 19/002

See application file for complete search history.

(56) References Cited

FOREIGN PATENT DOCUMENTS

| | | | | |
|---|---|---|---|---|
| JP | 2010229117 | * 10/2010 | .......... A61K 31/195 |
| JP | 2010229117 A | * 10/2010 | .......... A61K 31/195 |
| KR | 20130134532 A | 12/2013 | |
| KR | 20160107457 A | 9/2016 | |
| WO | 2006118245 A1 | 11/2006 | |

OTHER PUBLICATIONS

CN104983599A translation (Year: 2015).*

Skin and Liquid Crystal: A brief review on their similarities; Hamdan Suhaimi Laili et al; Aug. 2016Oriental Journal of Chemistry 32(4):2073-2078.

Ceramides and Skin Function; L. Coderch Et al; Feb. 2003American Journal of Clinical Dermatology 4(2):107-29 DOI: 10.2165/00128071-200304020-00004.

Suzuki, et al., "Development of Synthetic Ceramide-based Biomimetic Skin Care Products", The Chemical Society of Japan 1993 (10) 1107-1117 and English Abstract.

Blanton, et al., JCPDS-International Centre for Diffraction Data round robin study of silver behenate. A possible low-angle X-ray diffraction calibration standard, Powder Diffraction, 10(2):91-95 (1995).

Shrestha, Lok Kumar, Study of the Growth Control of Nonionic Surfactant Reverse Micelles by Water and Glycerol Using Small-angle X-ray Scattering, J. Nepal Chem. Soc., 24:12-18 (2009).

* cited by examiner a – Untreated1
b – Untreated2
c – Untreated3
d – Silverol1
e – Silverol2
f – Silverol3
g – A Composition1
h – A Composition2
i – A Composition3

Temperature (°C)

Control    1 hr    3hr    48hr    72hr

Time After Thermal Insult

N2          S1          D1          N1

S3          D3          N3          S2          D2

METHODS AND COMPOSITIONS FOR TREATING AND PREVENTING SKIN BARRIER DISRUPTIONS

FIELD OF THE INVENTION

The present invention relates generally to topical insult treatments, and preventive methods, and more specifically to methods of producing compositions for treatment of, and protection from, skin barrier disruptions, skin insults and skin conditions.

BACKGROUND OF THE INVENTION

Our skin is the largest organ in the body and it serves multiple critical functions. Due to the existence of the "skin barrier", the skin regulates the body temperature, prevents fluid loss by evaporation, and functions against infection. It also contains the sensory receptors that provide vital information about the environment.

The skin barrier is in fact the stratum corneum (SC), which is the outermost layer of the epidermis. The stratum mal, UV or other irradiation insults damage the skin through a similar pathophysiological process. Heat on skin layers can also form from skin inflammation and skin dehydration leading to skin-barrier disruption. Skin barrier disruption can also cause inflammation (e.g. insect bite, dermatitis) and dehydration (e.g. xerosis).

Although deep skin layers may be destroyed immediately following exposure to severe insults, in most cases, the stratum corneum/"skin barrier" is the first to be damaged. Deeper skin layers may then be involved, because of a "domino effect", originating from the skin barrier disruption.

The severity of a burn condition, or burn condition outcome, is a function of the intensity and duration of the insult (e.g. energy). For example, the temperature of the heat source and/or its duration on skin will determine the severity of the burn. The three main burn severity classifications are: superficial partial-thickness (first-degree), deep partial thickness (second-degree), and full thickness (third-degree).

Thermal-mechanical-radiation-laser- and other insult-mediated injury to the skin triggers a "domino effect" and a chain of events of wound progression, as summarized in the table 1 below:

TABLE 1

| Stage | Phase | Duration | Progression of Damage |
|---|---|---|---|
| 1 | Emergent | Minutes to hours | Pain response ⇨ adrenaline release⇨ heart rhythm irregularities ⇨ mild hypertension |
| 2 | Fluid Shift | 8-24 hours | Inflammatory response by damaged ⇨ cells cellular fluid shift ⇨ substantial edema (swelling, blistering) |
| 3 | Hypermetabolic | Days to weeks | Period of eschar and tissue healing |
| 4 | Resolution | | Scar formation, gradual return to normal tissue function | corneum functions to form a barrier to protect underlying tissue from infection, dehydration, chemicals and mechanical stress. This layer is composed of dead or non-dividing keratinocytes termed corneocytes, mainly keratin protein embedded at a liquid crystal (LC) phase of a lipid matrix composed of phospholipids/ceramides, cholesterol, and fatty acids.

The liquid crystal phase per se of the stratum corneum enables skin's protection of the body's homeostasis. Concomitant to environmental or internal change in temperature, and thermal or any kinetic vibration of molecules, the components of the stratum corneum undergo "thermotropic phase transitions", and may slightly change the liquid crystal phase into a range of mesophases, allowing water loss (cooling by transpiration) or in a mirror situation, by prevention of water loss and maintenance of the body's temperature. The process of cooling, for example, involves removing of internal energy from the system. Thus, the stratum corneum itself, due to its liquid crystal state, functions as a phase changing material (PCM), having the capability to change phases with varying kinetic energies or thermal energies, and may elicit latent heat, thermal radiation, absorbance or maintenance.

A burn is an insult-mediated skin condition, damaging the "skin barrier" with disruption of the stratum corneum, caused by any energy applied to the skin including heat, radiation, laser, radioactivity, extreme low temperatures, electricity, or mechanical abrasion, chafing and friction. Chemicals can also be a source of burns simply by a chemical-mediated disruption of the stratum corneum. Ther- If the burn injury is allowed to progress through to the metabolic and inflammatory stages described above, the risk of complications—primarily from fluid loss and infection—increases exponentially. Complications associated with burn injuries can arise despite application of existing early burn management, and even low intensity treatment for a moderate burn can cost $200,000 per treatment or more if there are complications.

Although there are no exact statistics on how many people experience burns (of any kind), we do know that, worldwide, at least 6,000,000 patients seek treatment for burn injuries each year, making burns a severe burden on healthcare systems. In 2015 in the US alone, 486,000 patients received hospital and emergency room treatment for burns, the vast majority of which occurred at home or in the workplace. Of these, 50,000 required hospitalization and treatments that cost more than $10.4 billion.

The current state-of-the-art burn care treatments, which aim to cool the affected area and to increase hydration by water/hydrogel- or alcohol-based formulations, to prevent contamination and infection (e.g. silver-based formulations), to reduce pain by analgesics/anesthetics and to support wound healing (e.g. enzyme- and cell-based formulations), involve a large regiment of different treatments for each phase of the chain reactions known until now to follow the initial insult. It requires a range of professionals, from daily nursing to hospitalization with enrollment of surgeons, dermatologists, psychologists, occupational therapeutics etc.

In the case of more severe burns, reparative treatment often involves the destruction of part of the damaged epithelial layer, including cutting out blisters (bullae) and the removal of adherent necrotic (dead) tissue and eschar (debriment). These treatments are associated with numerous complications due to loss of the epithelial barrier, and can cause irreparable scarring. If they are not effective, it may be necessary to replace irreparably damaged skin through grafting and skin substitutes.

A significant number of burn patients die due to infection, dehydration, lack of healing and sepsis. Moreover, many burn patients have disabling wounds and scars, years after the initial burns. Additionally or alternatively, the patients may be disfigured and require plastic surgery.

It is therefore an object of the present invention to provide a topical composition for preventing, treating, alleviating, and/or attenuating a skin barrier disruption in a subject.

It is another object of the present invention to provide a pharmaceutical composition, and/or a pharmaceutical "carrier" for treating a subject suffering from a skin barrier disruption.

SUMMARY OF THE INVENTION

In one aspect, the present invention provides a lyotropic liquid crystal composition, comprising: (a) at least one phase changing material (PCM); and (b) at least one stratum corneum (SC) component, for topical administration in treating, attenuating, or preventing, a skin barrier disruption in a mammal.

In some embodiments, the lyotropic liquid crystal composition is in a phase selected from a hexagonal phase, a lamellar phase, a cubic phase, an inverse topology lyotropic phase, and any combinations thereof.

In some embodiments, the phase changing material (PCM) is a paraffin hydrocarbon, a fatty acid, a fatty acid salt hydrate, a phospholipid fatty acid salt hydrate, polyethylene glycol (PEG), a polyalcohol, a mineral oil, a hygroscopic material, an inorganic salt hydrate, and a combination of a fatty acid with sodium acetate trihydrate.

In some embodiments, the stratum corneum (SC) component is selected form a phospholipid, cholesterol, free fatty acid, squalane, n-alkane, a triglyceride, ceramide, keratinocyte-derived ingredient, protein, keratin, and a keratin-derived ingredient.

In some embodiments, the composition further comprises at least one amphiphilic compound, a surfactant, and a solvent selected from water, an aqueous phase, or a non-aqueous phase.

In some embodiments, the composition further comprises at least one additive selected from a vitamin, a sunscreen, a di-glyceride, a tri-glyceride, an antibiotic, an antifungal, citric acid, an insect repellent, an analgesic, an active cosmetic ingredient, a polyol, a disinfectant, an astringent, an herbal extract, a fruit extract, a preservative, a pigment, a thermotropic liquid crystal pigment, an oil, a etheric oil, a perfume, a scent, an anesthesia, an abrasive and an emulsifier.

In another embodiment, the composition further comprises a drug.

In still another embodiment, the invention provides a composition for cosmetic use.

In some further embodiments, the composition of the invention is soap, soap-based composition, skin-protectant fire extinguisher or a skin-protectant fire extinguisher-based composition.

In some embodiments, the skin barrier disruption according to the invention is selected from a dermal insult, a topical insult, a skin disorder, a skin energy disruption, a skin ailment, a skin allergy, a skin discomfort, a skin discoloration, a skin perturbation, a superficial burn, a partial deep burn, a deep burn, a blister, a hyperemia, a topical pain, a topical wound, a dermal inflammation and a scar after an acute or chronic insult, and an acute or chronic skin irritation. Said acute or chronic skin irritation is selected from irritation following a thermal skin injury, an insect bite, an abrasion, irradiation, laser, exposure to extreme low temperatures, acne, wrinkles, nurturing breast-skin damage, skin chafing, and skin dryness.

In some embodiments, the composition is adapted for preventing a skin barrier disruption selected from a dermal medical procedure, a veterinary dermal procedure, sanitary preparation for medical purposes, preparation for hygienic purposes, soap, preparation for destroying fungi or vermin.

In some embodiments, said topical administration is selected from applying, applying as a soap, smearing, or spraying the composition, with or without a dressing, directly onto the skin barrier disruption, or on fabric wipes, paper wipes, silicon pads, band aids, or bandages.

In another aspect, the present invention provides a method for treating, attenuating, or preventing a skin barrier disruption in a mammal, the method comprising administering a composition comprising (a) at least one phase changing material (PCM); and (b) at least one stratum corneum (SC) component, to a skin barrier disruption.

In still another aspect, the present invention provides a method of reducing the scarring of a skin area following a skin barrier disruption, the method comprising, applying a composition comprising (a) at least one phase changing material (PCM); and (b) at least one stratum corneum (SC) component, to a local area of skin in a vicinity of said skin barrier disruption.

In a further aspect, the present invention provides a method for producing a lyotropic liquid crystal composition in accordance with the present invention, the method comprising: (a) hydrolyzing and/or saponifying and/or solubilizing at least one PCM component and at least one SC component to produce an amphiphilic product; (b) hydration of said amphiphilic product; and optionally (c) adding at least one additive. According to a specific embodiment, the PCM is a fatty acid salt hydrate, or a phospholipid fatty acid salt hydrate.

In a yet further aspect, the present invention provides a lyotropic liquid crystal composition, comprising (a) at least one phase changing material (PCM); and (b) at least one stratum corneum (SC) component, for use in treating, attenuating, or preventing, a skin barrier disruption in a mammal.

BRIEF DESCRIPTION OF THE DRAWINGS

The invention will now be described in connection with certain preferred embodiments with reference to the following illustrative figures so that it may be more and fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1A is a simplified block diagram of insult-induced damage and repair mechanism to a skin barrier, in accordance with an embodiment of the present invention;

FIG. 1B is a simplified schematic flowchart of a summarized method for preparing a formulation for dermal application, in accordance with an embodiment of the present invention;

Figures 2A, 2B:
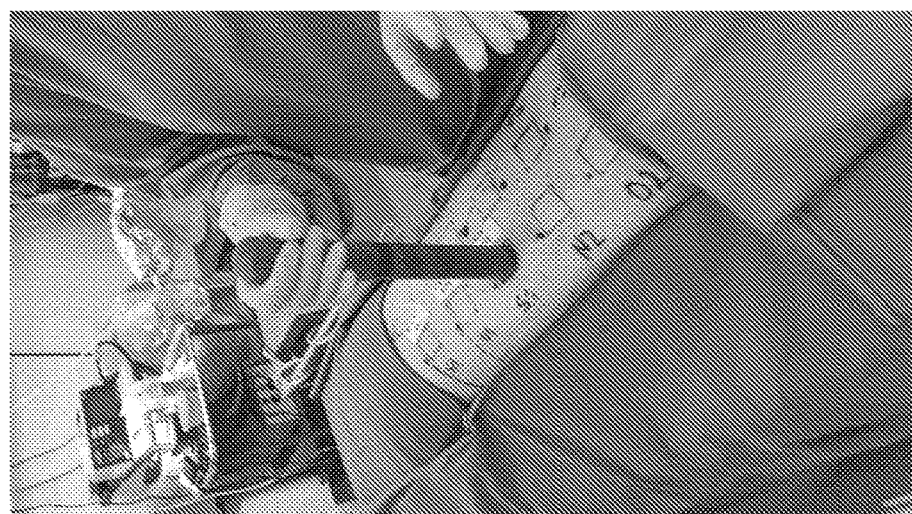
Figure 3A:
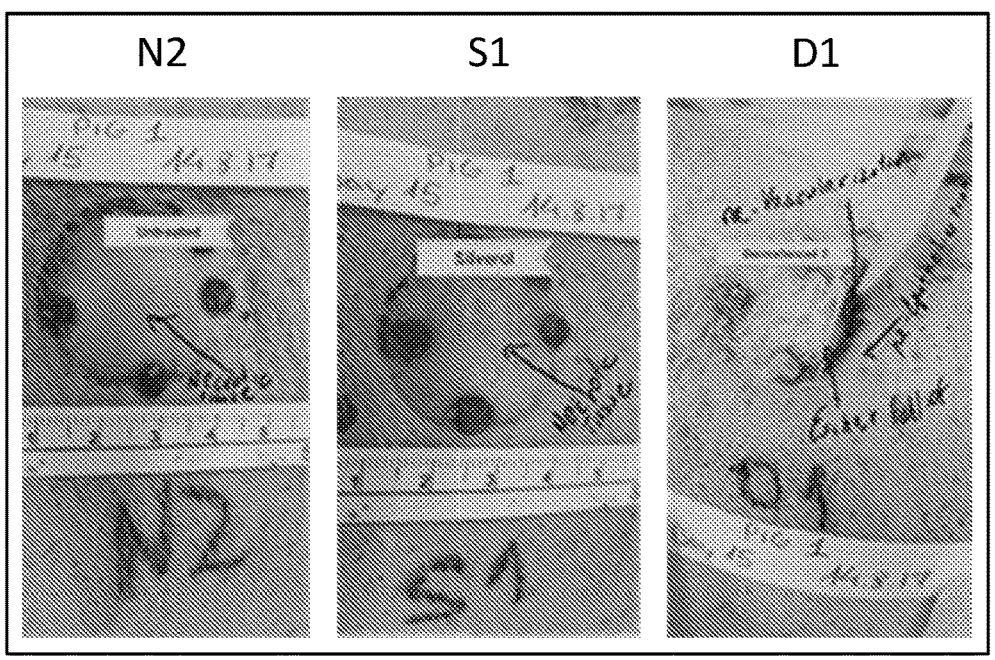

FIG. 2A is an image of a dermal dorsal burn insult tool, a 300 mm brass rod stick, applied under sterile conditions on a 3 month old pig. Spots of burns on skin are marked for: no application (N1, N2, N3) of a formulation (No treatment), application of control-treatment, silver-based, Silverol (S1, S2, S3), and application of A Formula (D1, D2, D3) in accordance with an embodiment of the present invention;

FIG. 2B is graphical presentation of temperature measures (° C.) of 9 dermal dorsal spots before (control), and after burn insults, on 3 month old pigs following 1 hr, 3 hrs., 24 hrs., and 72 hrs., without application of a formulation ("Untreated"), with application of control-, silver-based treatment ("Silverol"), and with application of the composition of the invention ("A Composition");

FIG. 3A is an image of a dermal dorsal burn insult on a 3-month-old pig following 15 days' time without application (N2) of a formulation (No treatment); with application of control, silver-based treatment, Silverol (S1); and with application of A Formula (D1) in accordance with an embodiment of the present invention.

Figure 3B:
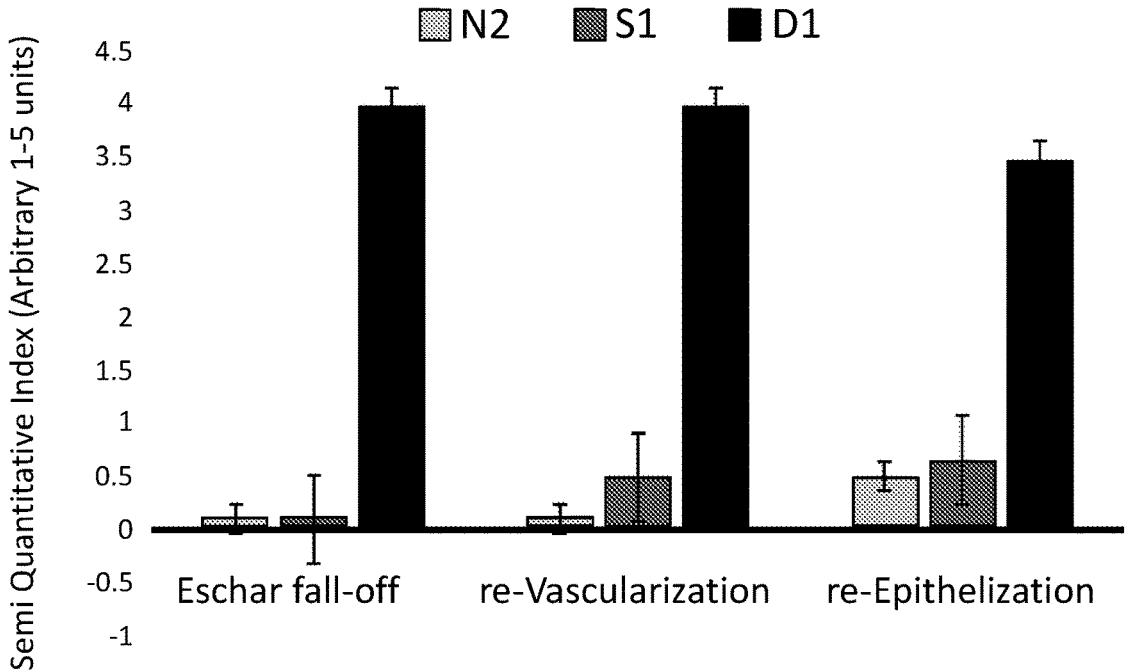

FIG. 3B is graphical presentation of 18 dermal dorsal burn insults on two 3 month old pigs following 15 days' time without application of a formulation "No treatment"; with application of control, silver-based treatment, "Silverol"; and with application of "A Formula" in accordance with an embodiment of the present invention.

Figure 4A:
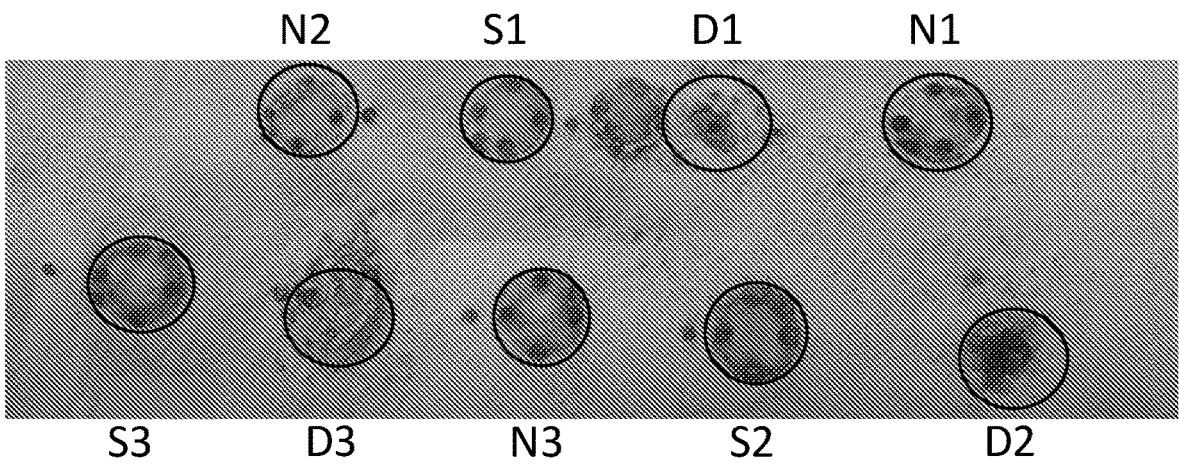

FIG. 4A is an image of a dermal dorsal burn insult on a 3 month old pig following 18 days' time without application (N1, N2, N3) of a formulation (No treatment); with application of control, silver-based treatment, Silverol (S1, S2, S3); and with application of A Formula (D1, D2, D3) in accordance with an embodiment of the present invention.

Figure 4B:
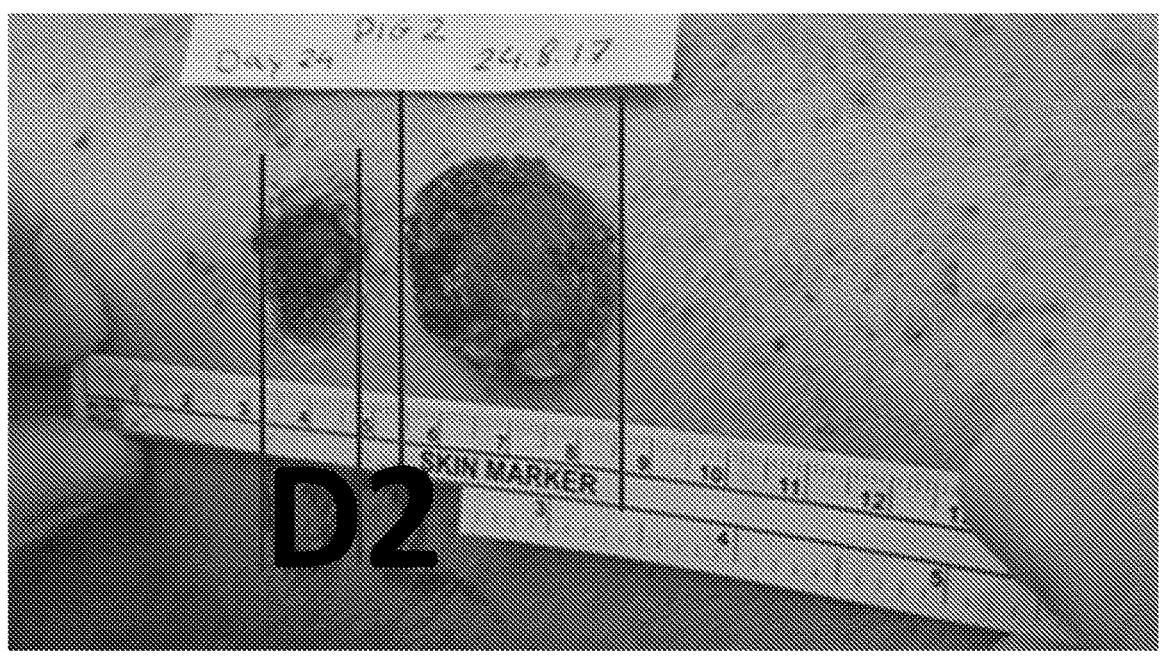

FIG. 4B is an image of a dermal dorsal burn insult on a 3-month-old pig following 24 days', with skin marker on insult spot and on fallen eschar (right hand side), with application of A Formula (D2) in accordance with an embodiment of the present invention.

Figure 4C:
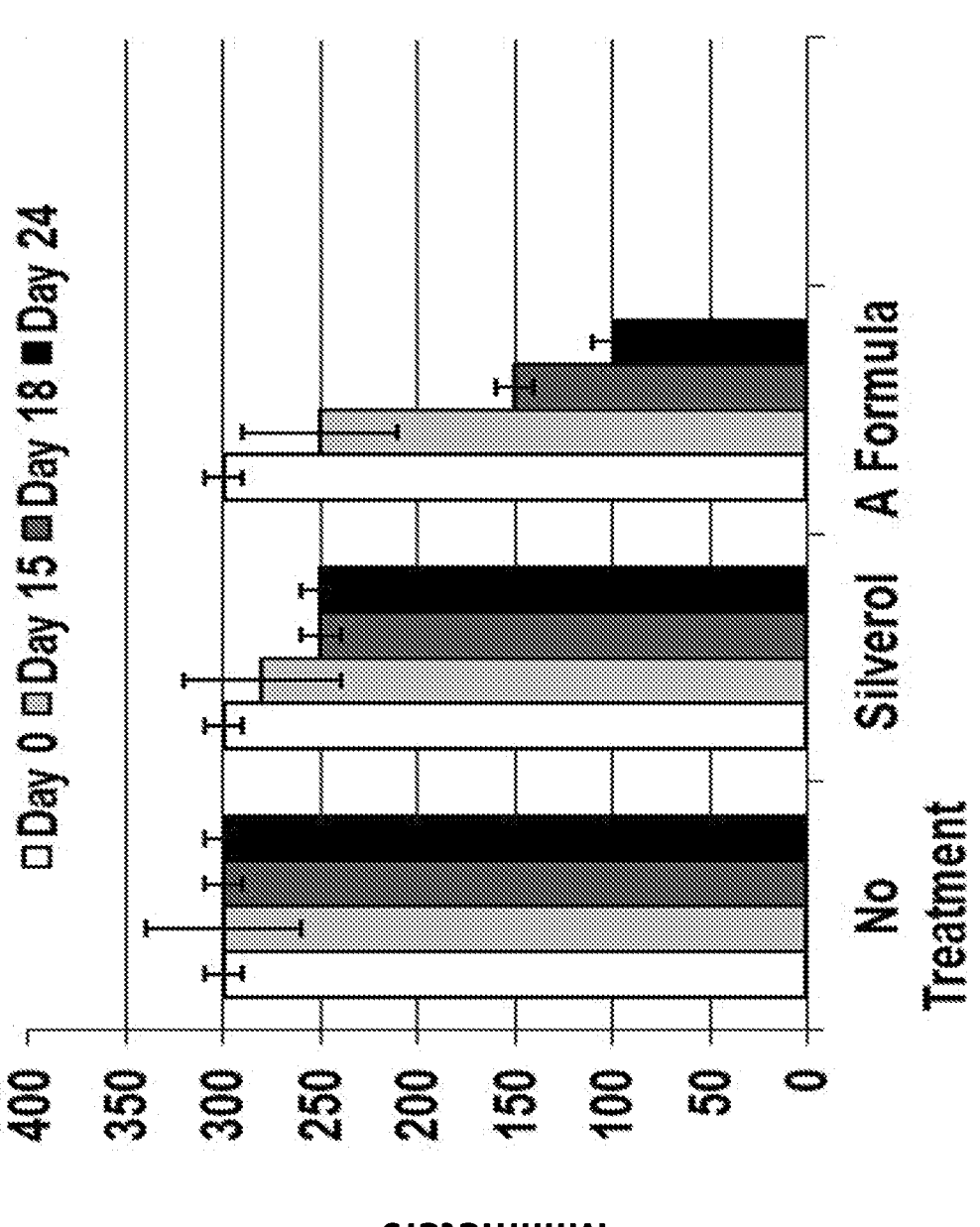

FIG. 4C is graphical presentation of diameter measures (millimeters) of 18 dermal dorsal burn insults on 3 month old pigs following 15, 18 and 24 days' compared to day 0 time, without application of a formulation "No treatment"; with application of control, silver-based treatment, "Silverol"; and with application of "A Formula" in accordance with an embodiment of the present invention.

Figure 5:
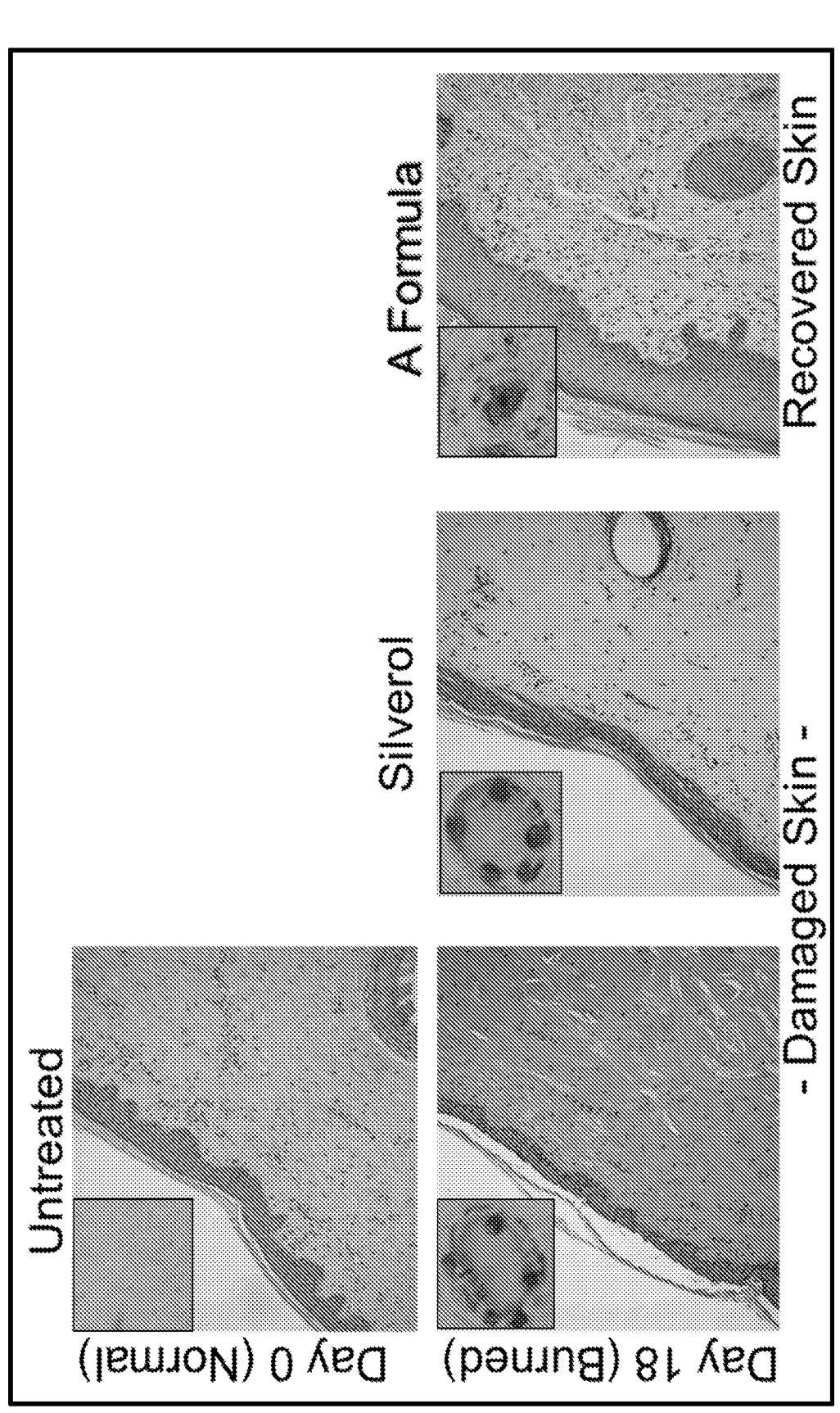

FIG. 5 is a light microscope image of skin-sections, and camera photographs (inserts) of dermal dorsal burn insults on a 3 month old pig following 18 days' compared to day 0 time, without application of a formulation "Untreated"; with application of control, silver-based treatment, "Silverol"; and with application of "A Formula" in accordance with an embodiment of the present invention.

Figure 6A:

FIG. 6A is an image of a dermal UV insult on an 11 year old boys' shoulder. The image was taken 4 days' time following UV insult, without application (control) of a composition in accordance with an embodiment of the present invention.

Figure 6B:
Figure 7A:
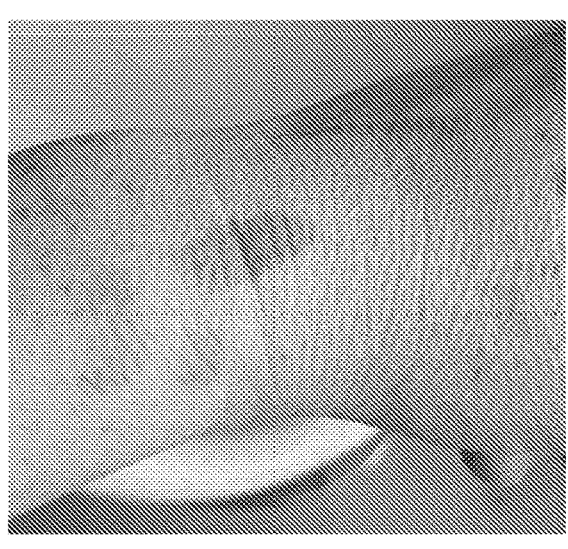
Figure 7B:
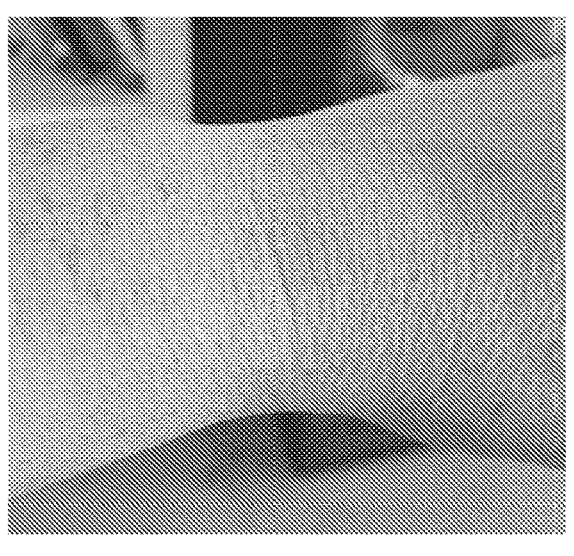

FIG. 6B is an image of a dermal UV insult on an 11 year old boys' shoulder. The image was taken 46 h time after application of a composition in accordance with an embodiment of the present invention;

FIG. 7A is an image of a subject with dermal thermal (scald from boiling oil) insult on a 48 year old lady arm 5 hour after the insult and application of a composition in accordance with an embodiment of the present invention;

FIG. 7B is an image of a dermal thermal (scald from boiling oil) insult on a 48 year old lady arm following 4 days' time after application of a composition in accordance with an embodiment of the present invention.

Figure 7C:
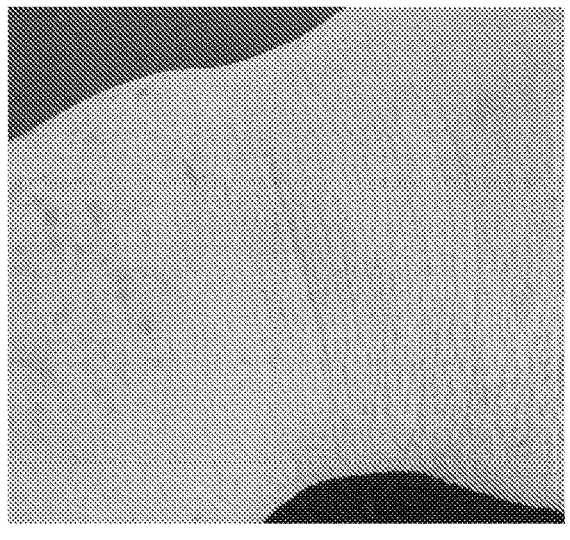

FIG. 7C is an image of a dermal thermal (scald from boiling oil) insult on a 48 year old lady arm following 7 days' time after application of a composition in accordance with an embodiment of the present invention.

Figure 8A:
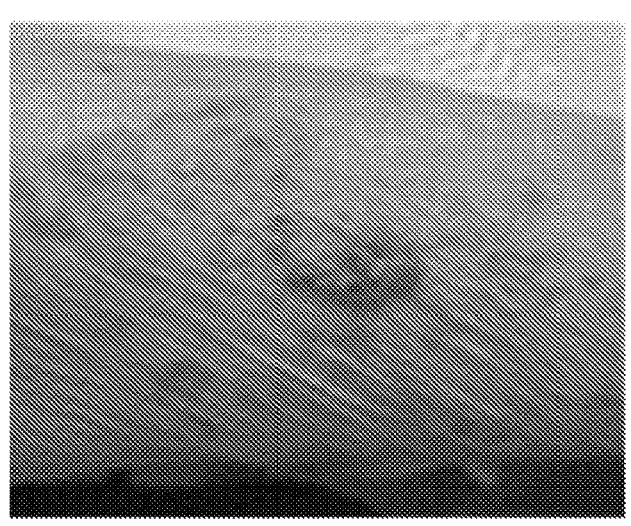

FIG. 8A is an image of a dermal Xerosis on an 85 year old lady arm without application (control) of any composition.

Figure 8B:

FIG. 8B is an image of a dermal Xerosis on an 85 year old lady arm following 2 weeks' time after application of a composition in accordance with an embodiment of the present invention.

Figure 8C:
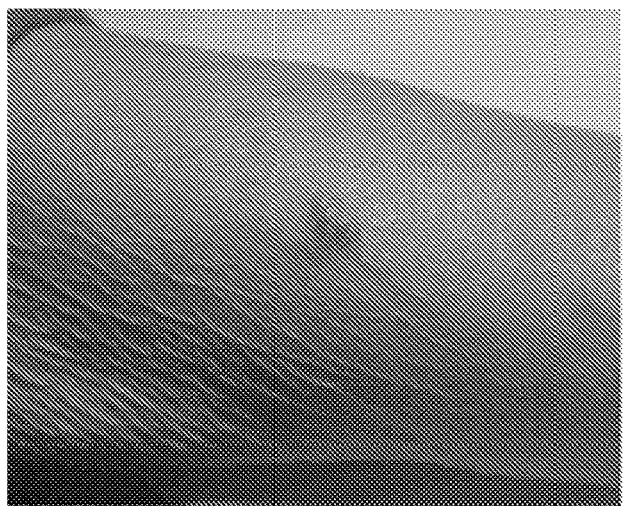

FIG. 8C is an image of a dermal Xerosis on an 85 year old lady arm following 4 weeks' time after application of a composition in accordance with an embodiment of the present invention.

Figure 9:
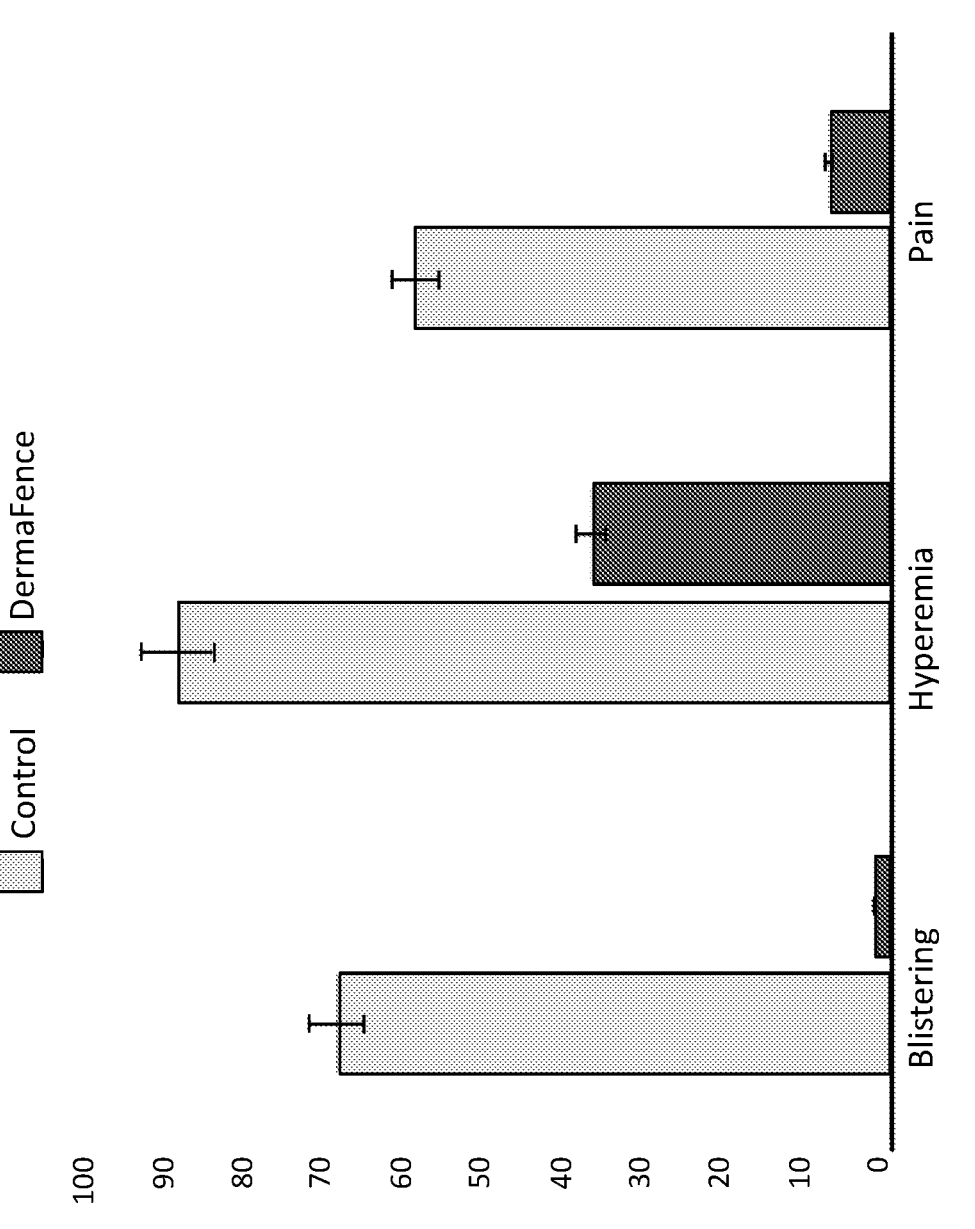

FIG. 9 is a graph of relative extent of blistering, hyperemia and pain (percentage) of subjects (n=18) without treatment and subjects after treatment with a topical composition in accordance with an embodiment of the present invention.

In all the figures similar reference numerals identify similar parts.

DETAILED DESCRIPTION OF THE INVENTION

In one aspect, the present invention provides a lyotropic liquid crystal composition, comprising: (a) at least one phase changing material (PCM); and (b) at least one stratum corneum (SC) component, for treating, attenuating, or preventing, a skin barrier disruption in a mammal.

Phase changing materials (PCMs) are well known to have the capacity to absorb and accumulate heat while changing from solid (crystal) to liquid and later release this latent heat while returning to solid (crystal) phase as they cool. The uniqueness of PCMs is that during such phase changes, the temperature of the PCMs themselves remains nearly constant and so does the space surrounding them.

High concentration of fatty acid salts, fatty acid salt hydrates, surfactants, amphiphilic compounds or molecules and others crystallize into a lamellar and hexagonal and other mesophases of liquid-crystal structures, that may mimic stratum corneum, skin barrier and membranes in biological systems.

Liquid crystals are characterized as optically anisotropic compounds between the crystal/solid phase and the isotropic liquid phase with a fluidity of liquids, but an average structural order relative to each other along the molecular axis as a solid, transmitting polarized light (birefringence) under static conditions. In other words, liquid crystals possess liquid-like fluidity but the molecules are oriented in a crystal-like manner. Many compounds are known to form a liquid crystalline mesophases. They can be natural or synthetic, high molecular polymeric amphiphile or non-amphiphile liquid crystals or low molecular weight as organic surface active amphiphile liquid crystals. The range of liquid crystal mesophases is influenced either by changes in temperature (thermotropic liquid crystal) or by changes in concentration in a solvent (lyotropic liquid crystal). At low concentrations, an amphiphilic compound or molecule, for example, forms an isotropic phase. However, as its concentrations in solvent increase, a gradually liquid crystal phase is formed in the isotropic phase until a homogenic and anisotropic liquid crystal is acquired. Increments in concentrations occurring, either following its addition or following evaporation/drying process, will further lead to a mixture of liquid crystal (lyotropic crystal) and crystal phase up to total crystallization. These are examples of endothermic change in phase. Upon rehydration/solvent absorption, an exothermic process occurs. These effects of enthalpy are in some cases similar to a PCM.

Accordingly, the term "lyotropic liquid crystal" refers to a mesophase that is formed by dissolving or emulsifying an amphiphilic molecule in a suitable solvent, under appropriate conditions of concentration, temperature and pressure. A mixture of high soap concentration in water is an example of a lyotropic liquid crystal. The amphiphilic molecules or compounds comprise a hydrophilic head-group (which may be ionic or non-ionic) attached to a hydrophobic group. Lyotropic liquid crystals have an additional degree of freedom that is the concentration that enables them to induce a variety of different phases. As the concentration of amphiphilic molecules is increased, several different types of lyotropic liquid crystal structures occur in solution. Each of these different types has a different extent of molecular ordering within the solvent matrix. The lyotropic liquid crystal according to the present invention may form the structure of a hexagonal phase, a lamellar phase, a cubic phase, an inverse topology lyotropic phase, or any combinations thereof. Accordingly, in some embodiments of the present invention, the liquid crystal phase is selected, but not limited to a hexagonal phase, a lamellar phase, a cubic phase, an inverse topology lyotropic phase and combinations thereof.

To tentatively mimic the skin barrier and stratum corneum (e.g. lamellar liquid crystal), the fatty acid, fatty acid salt, fatty acid salt hydrate, liquid crystal-forming materials and/or lipids, require minimum water content for stability, and can function also as a PCM or as a carrier for PCMs which tend to disperse upon phase changing. Below that water concentration, liquid crystals form. In addition, PCM and/or stratum corneum components can be formulated to form a liquid crystal phase and/or be part of and/or be intercalated in materials forming liquid crystals.

The immediate beneficial effects of PCMs at a liquid crystal (LC) mesophases on skin barrier disruptions, such as burned skin, skin irritations, wounds and other skin conditions, appear to be related to cooling by an endothermic phase transition and by supporting skin barrier.

Thus, in one aspect, the present invention provides a lyotropic liquid crystal composition, comprising: (a) at least one phase changing material (PCM); (b) at least one stratum corneum (SC) component, for treating, attenuating, or preventing, a skin barrier disruption in a mammal.

In some embodiments, the lyotropic liquid crystal composition of the invention comprises between 10% to 60% w/w water, based on the total weight of the composition.

In some embodiments, the present invention provides a composition for treating, or attenuating, or preventing, and/or protecting from, skin barrier disruptions, such as topical insults, to a local area of mammalian integumentary system, and the skin in particular. The composition, including at least one phase changing material and at least one stratum corneum component, is adapted to absorb and transfer energy (e.g. heat) from the skin area, in order to treat the skin barrier disruption, and protect from an insult.

There is thus provided according to an embodiment of the present invention, a composition for topical application for treating, or attenuating and/or protecting from, a dermal insult on a local area of skin of a mammal, the composition including (a) at least one phase changing material (PCM); and (b) at least one stratum corneum (SC) component; wherein the composition is adapted to absorb energy (heat) from the local area to treat, or attenuate and/or to protect from, a dermal insult.

According to some embodiments, the composition comprises one PCM, two PCMs or up to 20 PCMs, specifically at least one PCM selected of the 5 PCM groups as defined herein.

According to some embodiments, the composition comprises one stratum corneum (SC) component, two stratum corneum (SC) components or up to 20 stratum corneum (SC) components. According to a specific embodiment, the composition comprises five, six or seven stratum corneum (SC) components.

It should be noted that in some cases, a stratum corneum (SC) component can act as a phase changing material (PCM). In such cases, the composition of the invention comprises only a single active compound, which serves both as a stratum corneum (SC) component and as a phase changing material (PCM), and is able to provide a composition having the desired properties.

A PCM may be characterized by absorption or release of 50-200 J/g heat during the solid-solid (solid-liquid crystal) and solid-liquid phase transition.

According to some embodiments, the PCM is a single compound or a mixture of compounds selected from the group consisting of: Paraffin hydrocarbons, Non-paraffin compounds, hygroscopic materials and Eutectic PCM compounds.

Paraffin hydrocarbons include mineral oil products and normally consist of straight chains of n-alkanes $CH_3$—$(CH_2)_n$—$CH_3$ or, more in general, $(C_nH_{2n+2})$ with $n \geq 16$. As the length of the chain increases, so does the melting temperature heat of fusion (HoF) or latent heat, which has a tendency to increase with the number of carbon atoms composing the chain. Paraffins are safe, reliable, predictable and non-corrosive. Paraffin wax is generally a mixture usually composed by different alkanes.

Non-paraffin compounds include Fatty acids, Salt hydrates, Glycols and Polyalcohols.

Fatty acids (FAs), are characterized by the general chemical formula $CH_3(CH_2)_{2n}COOH$.

Fatty acid eutectic mixtures have a better heat reliability and the binary and ternary fatty acid eutectic mixtures have lower phase change temperatures with respect to the correspondent single fatty acid. Fatty acid eutectic mixtures include higher monocarboxylic acids having from about 12 to about 22 and 8 to 25 carbon atoms. Saturated or unsaturated, substituted or unsubstituted fatty acids or combinations thereof are useful. The melting points of saturated fatty acids increase gradually with their molecular weights.

Salt hydrates are alloys of salt and water $AB_nH_2O$, such as fatty acid salt hydrates, and inorganic salt hydrates $M_nH_2O$ e.g. copper salt hydrate.

Of note, fatty acids can form salt following neutralization with, for example, an alkali (e.g., zinc oxide, metal hydroxide as sodium hydroxide, magnesium hydroxide, aluminum hydroxide).

Glycols, with the common name Polyethylene glycols (PEGs), are defined by the general chemical formula $HO-CH_2-(CH_2-O-CH_2-)n-CH_2-OH$. Glycols are soluble in water and in organic compounds. With the increase of the average molecular weight (MW) of the compound, the melting temperature HoF increases.

Polyalcohols, along with some specific polyalcohol amine derivatives, are PCMs characterized by a relatively low enthalpy of fusion. Despite this, they are able to release and absorb a large amount of heat during a solid-solid or liquid crystal mesophases transitions. For example, PEGs undergo phase transition at temperatures ranging from 15° C. to 60° C.

A hygroscopic material can absorb and release water in parallel to absorbing or releasing heat. For example, cellulose, keratin.

An Eutectic PCM, may be a combination of a PCM, such as a fatty acid with sodium acetate trihydrate.

Accordingly, the phase changing material (PCM) according to the present invention may be a paraffin hydrocarbon, a fatty acid, a fatty acid salt hydrate, a phospholipid fatty acid salt hydrate, polyethylene glycol (PEG), a polyalcohol, a mineral oil, a hygroscopic material, an inorganic salt hydrate, and a combination of a fatty acid with sodium acetate trihydrate.

According to some embodiments, the composition of the invention comprises a fatty-acid salt hydrate, which is an organic salt hydrate, able to absorb well heat over 200 kJ/kg. The PCM optionally further comprises a paraffin oil, having a thermal conductivity of 10 to 400 W/m*k.

One compound, or a mixture of two or more compounds, can function as the PCM component in the composition of the invention.

According to some embodiments of the present invention, the at least one PCM is present in the composition in a concentration of 0-90%, more specifically 50-70% by weight percent.

According to some further embodiments, the stratum corneum (SC) component is a single compound or compounds mixture/s selected from the group consisting of: lipids, glycerides, fatty acids, squalene, squalane, phytosqualene, sterols (such as phytosterols, cholesterols, lanolin and others), keratinocyte-derived ingredients, proteins, keratins and a keratin-derived ingredients. The stratum corneum (SC) component includes:

Non Polar lipids: obtained from Sterols/wax esters, as beeswax and/or n-alkanes.

Phospholipids: hydrogenated or hydroxylated, lecithin, phytosphingosine, ceramides, sphingosine, sphinganine and phytosphingosine, and mixtures thereof. In terms of oxidative stability, the phospholipids that are hydrogenated or hydroxylated with an iodine value of around 20 are preferred. Even if present at an amount of as low as 1 Wt % in the lipid lamellar of the stratum corneum, phytosphingosine is very important because of its antimicrobial activity. In addition, phytosphingosine is a precursor for ceramides.

Triglycerides as fats or oils (e.g., palm, coconut, olive, neem, pomegranate, avocado and all others existing).

Fatty acids (FAs) and free fatty acids (FFAs)—carboxylic acids. Saturated or unsaturated fatty acids containing 8-25 carbon atoms or combinations thereof are used (e.g. Myristic, Palmitic, Palmitoleic, Stearic, Oleic, Linoleic, Arachidic and all others existing). Higher monocarboxylic acids having preferably from about 12 to about 22 carbon atoms. Saturated or unsaturated, substituted or unsubstituted fatty acids.

One stratum corneum compound, or a mixture of two or more compounds, can function as the stratum corneum component in the composition of the invention.

Among the SC components, the composition may contain sphingolipid/s and/or phospholipid/s and/or phosphatidylcholine, such as lecithin and/or ceramide/s (0-90%, specifically 15-25%), sterols such as phytosterol/s, lanolin, cholesterol (0-90%, specifically 10-20%), wax esters such as beeswax, carnauba wax (0-90%, specifically 4-8%), alkenes such as n-Alkanes as camellina wax/oil (0-90%, specifically 2-7%), Squalene and/or phytosqualene (squalane) (0-90%, specifically 4-8%), free fatty acid/s (FFA) (0-90%, specifically 0.01-15%).

In some embodiments, the composition may contain the following free fatty acid/s (FFA): stearic acid (e.g., 9.9%), Myristic acid (e.g., 3.8%), Arachidic acid (e.g., 0.3%), linoleic acid (e.g., 12.5%), palmitic acid (e.g., 36.8%), palmitoleic acid (e.g., 3.6%), oleic acid (e.g., 33.1%). Other FFAs may be included as well.

Accordingly, the stratum corneum (SC) component of the present invention may be selected form a phospholipid, cholesterol, a free fatty acid, squalane, n-alkane, a triglyceride, ceramide, keratinocyte-derived ingredient, a protein, keratin, and a keratin-derived ingredient.

According to some embodiments of the present invention, the at least one stratum corneum (SC) component is present in the composition in a concentration of 0-90%, more specifically, 50-70% by weight percent.

According to some embodiments, the composition of the invention further comprises at least one additive selected from the group consisting of: a drug, a vitamin (e.g., vitamin A, C, D, E and K), a sunscreen, a di-glyceride, a tri-glyceride, an antibiotic, an antifungal, citric acid, lactic acid, an insect repellent, an analgesic, an active cosmetic ingredient, a polyol, a disinfectant, an astringent, an herbal extract, a fruit extract, a preservative, a pigment, a thermotropic liquid crystal pigment, a lipid, an oil, a etheric oil, a perfume, a scent, an anesthesia, an abrasive and an emulsifier.

Accordingly, the compositions of the invention may include various drugs such as triethanolamine, trolamine/sodium alginate; anti-inflammatory as steroids; up to 2.5% hydrocortisone; anti-histamines; 0.1-3% Coal tar, benzoyl peroxide; 0.1%-3% antimicrobial/fungal agent (e.g. Silver-based components as 0.1-2% Silver Sulfadiazine or 0.1-2% bifonazole); 0.3-2% miconazole nitrate, and others; 3,4 di- and 3, 4', 5 tri-bromosalicylanildes; 4, 4' dichloro-3 (trifluoromethyl) carbanilide; 3,4, 4' trichlorocarbanilide and mixtures; sialic and glycolic acid; analgesics, e.g. lidocaine; and therapeutic enzymes.

The compositions of the invention may include alternate/talc and whitening materials, anti-static and skin conditioning, hyaluronic acid, hyaluronic acid compounds, collagen, milk extracts e.g. sine adipe lac, herbal materials, humectants, anti-oxidants and fillers, clay, honey, astringents as Zinc oxide, Zinc glycerolate, Zinc chloride, magnetic particles, minerals, gold particles, sodium, sodium chloride, chelating agents e.g. pentasodium pentetate, pentetic acid.

The compositions of the invention may include adjuvants selected from the group consisting of: water miscible or water soluble sunscreen agents or UV protectants e.g. benzyl salicylate; antioxidants e.g. pentaerythrifyl tetra-di-t-butyl hydroxyhydrocinnamate; insect repellents e.g. citronellol; chemical repellents; viscosity modifiers; D-Panthenol; hydrolyzed collagen; animal proteins, and any mixtures thereof.

According to some embodiments of the present invention, the at least one additive is present in the composition or formulation in a concentration of 0-30%, 1-20%, 2-15%, 3-10% by weight percent, based on the total weight of the composition.

According to some embodiments of the present invention, the composition further comprises at least one solvent or hydrant. In some cases, the hydrant is water, such as double-distilled water.

According to some embodiments of the present invention, the at least one solvent or hydrant is water, present in the composition in a concentration of 10-60%, specifically 20-40%, more specifically 30% by weight percent.

The solvent or hydrant may further comprise a pH regulator, such as an acid or base. In some embodiments, the base comprises sodium hydroxide and the acid, lactic acid.

A composition for topical application for treating, and/or preventing a skin barrier disruption, the composition comprising:

at least 40, 50, 60, 70, 80 or 90% w/w of at least one of and/or combinations thereof a saturated or unsaturated fat, a fat derivative, a lipid, a lipid derivative, a fatty acid, a saturated or unsaturated fatty acid, a fatty acid salt hydrate, a fatty acid ester, a fatty acid derivative, a fatty acid salt, a basic metal fatty acid, a basic metal fatty acid salt, a basic metal fatty acid salt derivative, an acidic metal fatty acid, an acidic metal fatty acid salt, an acidic metal fatty acid salt derivative, a sterol, a glycerol ester, an amphipathic lipid, a homo- and/or hetro-triglyceride, diglyceride, a monoglyceride, a triacylglycerol, a non-polar lipid, a glycerolphosphate ester, a glycerophosphatide, a phosphatidic acid, a phosphatidic acid derivative, phosphatidyl choline (also known as lecithin), phosphatidyl ethanolamine (also known as cephalin), phosphatidyl serine, phosphatidyl inositol, a phospholipid, a sphingolipid, a plasmalogene, a sterol, a sterol ester, a prenol lipid, a polyprenol, a prenol ester an alkane, a protein, a liposome a hygroscopic material. Lipids comprise a group of naturally occurring molecules that include fats, waxes, sterols, phytosterols, fat-soluble vitamins (such as vitamins A, C, D, E and K), Scientists may broadly define lipids as hydrophobic or amphiphilic small molecules; the amphiphilic nature of some lipids allows them to form structures such as vesicles, multilamellar/unilamellar liposomes, liquid crystals or membranes in an aqueous and non-aqueous solvent. Biological lipids originate entirely or in part from two distinct types of biochemical subunits or "building-blocks": ketoacyl and isoprene groups. Using this approach, lipids may be divided into eight categories: fatty acids, glycerolipids, glycerophospholipids, sphingolipids, saccharolipids, and polyketides (derived from condensation of ketoacyl subunits), sterol lipids, and prenol lipids (derived from condensation of isoprene subunits).

Although the term "lipid" is sometimes used as a synonym for fats, fats are a subgroup of lipids called triglycerides. Lipids also encompass molecules such as fatty acids and their derivatives (including tri-, di-, monoglycerides, and phospholipids), as well as other sterol-containing metabolites such as cholesterol.

In some embodiments, the present invention provides a lyotropic liquid crystal topical composition for treating, attenuating, or preventing, a skin barrier disruption, such as, a dermal insult, the formulation or composition comprising:

a. optionally 40, 50, 60, 70, 80 or 90% of an amphiphilic molecule having relatively no or little damage to skin barrier function;

b. optionally at least one of a liquid phase, selected from water, hydrocarbons or their mixtures, or non-aqueous solvent carrier of less than 60, 50, 40, 30 or 20, 10% w/w;

c. optionally at least one PCM, or a combination of PCMs, in a concentration of 0-90%, selected from organic and/or inorganic phase changing materials (PCMs) and fillers such as fatty acid/s, mineral oil/s such as paraffin), polyethylene glycol (PEG) such as PEG10 and hygroscopic material such as cellulose, keratin;

d. optionally at least one of a stabilizer, an emollient, a wax, an antiseptic, an antifungal, an antibiotic, an analgesic, an anti-inflammatory, an insect repellent, an humectant, an anesthetic, a mineral, an herb, a fruit, and their derivatives, a filler, an additive, a skin booster and a fragrance, a whitening agent, in a concentration of less than 15% w/w;

e. optionally 0-4% of an antibacterial as 3,4 di and 3,4',5 tribromosalicylanildes; 4,4' dichloro 3 (trifluoromethyl)carbanilide; 3,4,4' trichlorocarbanilide and mixtures of these materials;

f. optionally 10% to 60% of a solvent as aqua, as hydrocarbons, as propylene glycol, as glycerin, as their mixtures, as non-aqueous solvent, with or without herb/s and/or fruit/s and/or tree/s and/or flower/s extract/s, tincture/s, fusion/s such as meant, aloe, chamomile, centella and all others, vegetal and/or animal milk, honey;

g. optionally a protein, an amphipathic protein, a ceramide an amino acid;

h. optionally a skin component, a skin stratum corneum component, a skin barrier component and mimics and analogs;

i. optionally an alkane and n-alkanes;

j. optionally an aerosol propellant; and k. optionally a foaming/frothing chemical or mechanical factor, an hydrocarbon, a surfactant, a liquid crystal.

Compositions of the present invention may include PCM component/s (PEG, mineral oil, FFAs etc.) mixed with SC component/s (Cholesterol, squalane, n-alkanes, triglycerides, phospholipids etc.) in aqueous or non-aqueous media, emulsified, with preservative, pigment, analgesia, etc.

Compositions of the present invention may include PCM component/s (PEG, mineral oil, FFAs etc.) mixed with SC component/s (Cholesterol, squalane, n-alkanes, triglycerides, phospholipids, etc.) in aqueous or non-aqueous media emulsified with for example, lecithin, combined with xanthan gum liquid crystal, hygroscopic material, saponified hygroscopic material, preservative, pigment, analgesia, etc.

According to some additional embodiments of the present invention, PCM components (PEG, mineral oil, FFAs, etc.) mixed with SC components (Cholesterol, squalane, n-alkanes, triglycerides, phospholipids, keratin) are added to a FA salt purchased and/or derived from a neutralization and/or saponification process and partly from PCM and/or SC component/s. The mixture is further diffused with an aqueous or non-aqueous media which may also be absorbed by capillary forces to the FA salt which is rehydrated forming liquid crystal mesophases. PCM and/or SC component/s can be further added. A lyotropic liquid crystal phase is obtained, which may be emulsified with xanthan gum liquid crystal and combined with preservative, any drug category, humectant, pigment, analgesia and combinations thereof.

According to some additional embodiments of the present invention, the composition comprises lecithin (18%), lanolin (14%), beeswax (6%), alkenes such as n-alkanes (3.7%), squalane (6.5%), free fatty acids (19.3%). stearic acid (9.9%), myristic acid (3.8%), arachidic acid (0.3%), linoleic acid (12.5%), palmitic acid (36.8%), palmitoleic acid (3.6%), oleic acid (33.1%). zinc oxide (0.5%), mint tincture (6%), organic phase changing materials (PCMs)-PEG-10 (3%), paraffin (2%), and liquid crystal xanthan gum (20%).

Some aspects of the present invention provide a pharmaceutical composition for providing relief to a mammalian subject suffering from a skin insult.

Some aspects of the present invention provide a pharmaceutical composition for protecting a mammalian subject from a skin insult.

Some further aspects of the present invention to provide a pharmaceutical composition for treating a mammalian subject suffering from a skin insult.

Some additional embodiments of the present invention provide compositions and methods for treating, preventing, alleviating and/or to attenuating a skin barrier disruption in mammalian subject.

The skin barrier disruption according to the present invention is a dermal insult, a topical insult, a skin disorder, a skin energy disruption, a skin ailment, a skin allergy, a skin discomfort, a skin discoloration, a skin perturbation, a superficial burn, a partial deep burn, a deep burn, a blister, a hyperemia, topical pain, a topical wound, a dermal inflammation, a scar after an acute or chronic insult, and an acute or chronic skin irritation involving disruption of the skin barrier. The acute or chronic skin irritation is an irritation following a thermal skin injury, an insect bite, an abrasion, irradiation, laser injury, exposure to extreme low temperatures, acne, wrinkles, nurturing breast-skin damage, skin dryness, and skin chafing caused by sports, athletic activity, obesity, or army activity.

In some embodiments of the present invention, methods and compositions are provided for burn therapy.

In some embodiments of the present invention, methods and compositions are provided for therapy of chronic skin situations involving disruption of skin barrier.

In some further embodiments of the present invention, methods and compositions are provided for treating, preventing and/or attenuating blisters, hyperemia, pain, wound progression and subsequent scars after an acute insult to a mammalian's skin.

In some further embodiments of the present invention, methods and compositions are provided for preventing, treating, and/or attenuating blisters, hyperemia, pain, wound progression, inflammation and subsequent scars after a chronic insult to a mammalian's skin.

In some additional embodiments of the present invention, methods and compositions are provided for treating, attenuating and/or protecting from, superficial and/or partial deep burns and/or deep burns to a mammalian's skin.

In some still further embodiments of the present invention, methods and compositions are provided for preventing a skin barrier disruption selected from a dermal medical procedure, a veterinary dermal procedure, sanitary preparation for medical purposes, preparation for hygienic purposes, preparation for destroying fungi or vermin.

In some embodiments of the present invention, methods and compositions are provided for use as an additional component, or as the main component in artificial skin and skin complementing compositions.

Some embodiments of the present invention provide methods and compositions for use as "carrier" materials for drugs, anesthesia, analgesia, pro-hydration materials, collagen, urea, hyaluronic acid, UV protectant, insect repellent, anti-fungal, antibiotics, hair depilation compounds, anti perspirants, hair growth compounds, etc.

Some embodiments of the present invention provide methods and compositions for cosmetic use.

Some embodiments of the present invention provide methods and compositions for cosmetic use.

Some embodiments of the present invention provide a topical composition that is a first aid-treatment for treating a skin barrier disruption in a subject. This first-aid treatment is sufficient to treat a skin barrier disruption (i.e., a burn), without the need for any further medical procedures or therapies.

In one embodiment of the present invention, the composition is soap.

In one embodiment of the present invention, the composition is soap, soap-based composition, skin-protectant fire extinguisher or a skin-protectant fire extinguisher-based composition.

The mammalian subject according to the present invention may be human or animal.

Furthermore, according to some embodiments of the present invention, the composition is adapted to be applied, smeared, or sprayed directly onto the skin to treat, or attenuate and/or to prevent from, skin barrier disruption (i.e., a dermal insult).

Accordingly, the composition of the present invention is adapted to being applied, and/or smeared, and/or sprayed, and/or laid on as liquid crystal based emulsion, liquid crystal soap, liquid crystal based paste, liquid crystal based foam/mousse, liquid crystal based cream or liquid crystal based lotion, with or without a dressing, on area of skin around and/or on the dermal insult to treat, and/or protect from, said dermal insult.

Other embodiments of the present invention provide a medical device comprising a composition for treating, attenuating, preventing, and/or inhibiting irritation of a skin barrier disruption in a mammal, such as a wound following thermal injury, mechanical injury, radiation injury, laser injury, insect bites, abrasion, extreme low temperature injury, acne, wrinkles, skin dryness, and/or chronic skin conditions involving disruption of skin barrier.

The medical device according to the present invention includes medicated dressings, bandages, fabric wipes, paper wipes, silicon pads, and band aids that can be applied onto the skin in order to treat the skin barrier disruption.

There is thus provided according to an embodiment of the present invention, a method of treating, or attenuating and/or preventing skin barrier disruption (e.g., a dermal insult) in a subject, the method comprising, applying a composition, as described herein, to a skin area in a vicinity of the skin barrier disruption, thereby treating, and/or attenuating and/or preventing the skin barrier disruption, by lessening damage to the stratum corneum structure.

Additionally, according to one embodiment of the present invention, the composition is adapted to repair the stratum corneum structure.

Further, according to another embodiment of the present invention, the composition provides precursors, or stratum corneum structural elements, to repair the stratum corneum structure.

Yet further, according to an embodiment of the present invention, the composition is adapted to regenerate the stratum corneum structural elements.

Additionally, according to an embodiment of the present invention, the composition is adapted to mimic the stratum corneum structure and/or function.

Importantly, according to an embodiment of the present invention, the composition prevents or reduces scarring of the skin area in vicinity to the skin barrier disruption.

Additionally, according to an embodiment of the present invention, the composition induces healing of the skin area of a skin barrier disruption in a shorter time period than a non-treated skin area.

In a yet another embodiment, the composition prevents wound progression.

Additionally, according to an embodiment of the present invention, the composition induces eschar falloff from the necrotic (dead) skin area.

In another aspect, the present invention provides a lyotropic liquid crystal composition, as detailed herein, for use in treating, attenuating, or preventing, a skin barrier disruption in a mammal.

Figure 1A:
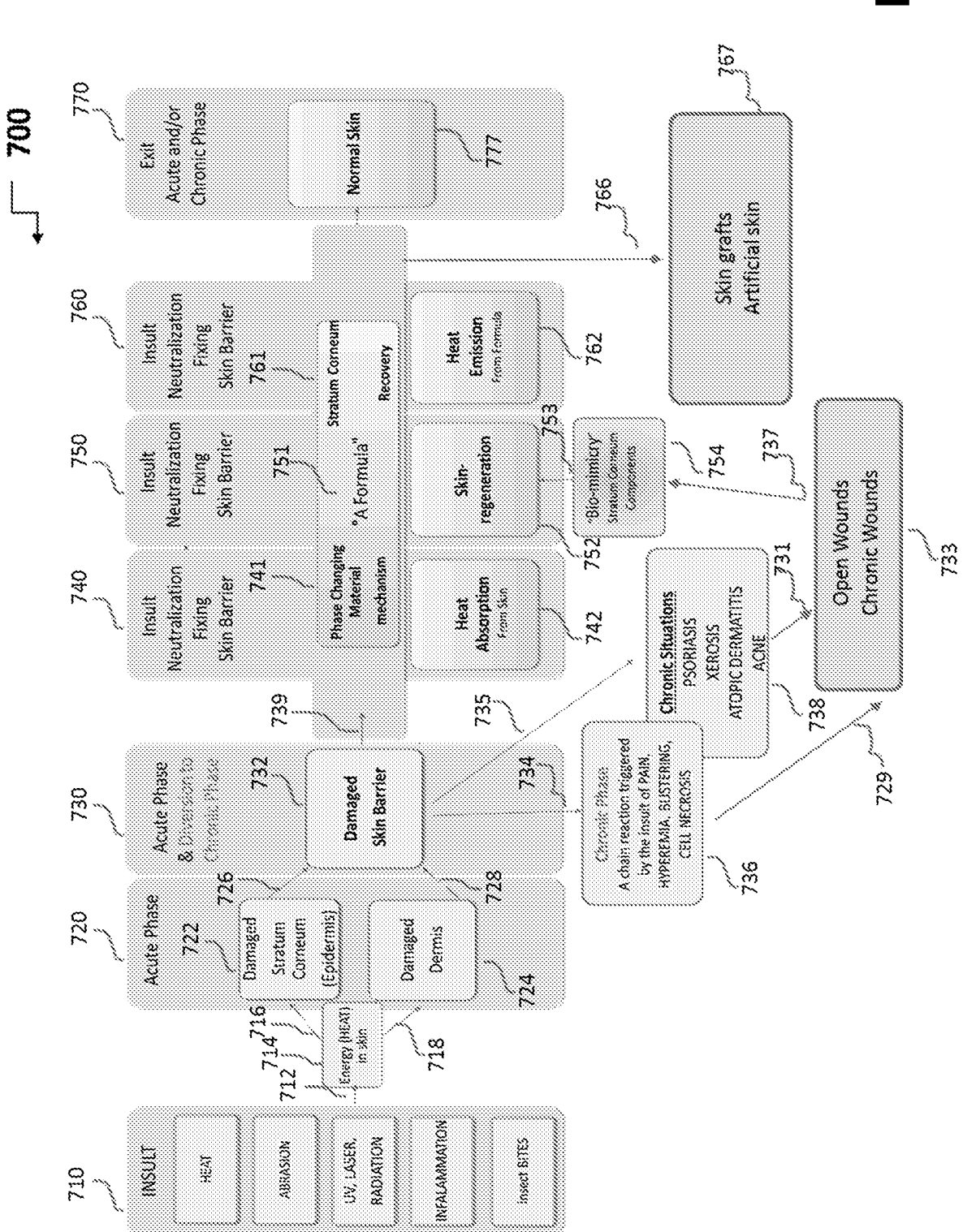

FIG. 1A shows a simplified block diagram of insult-induced damage to a skin barrier and repair mechanism of this invention. This figure describes the process of skin burns or other skin insults, application of the compositions of the present invention and skin repair thereafter. 700—an insult (heat/abrasion/UV/laser/radiation therapy/inflammation/insect bite/extreme cold etc.) (710), leads (712) to energy impinged on and in the skin (714) which further leads (716), (718) to an acute phase (720), which involves damage to different skin layers as the stratum corneum (SC) at the epidermis (722) and at the dermis (724). Damage to these skin layers lead to (726), (728) disruption of the skin barrier (732) and diversion from acute phase to a chronic phase (730) in a linear correlation to strength and/or insult duration. Usually this stage progresses to a chronic phase involving pain, hyperemia, blistering and, cell necrosis (736). Damage to skin barrier is known to initiate (735) chronic situations as psoriasis, xerosis, atopic dermatitis, acne etc. (738). Chronic situations as well as the chronic phase of insult-mediated damage may lead (731), (729) to the evolution of open and chronic wounds (733).

In contrast, when the skin is exposed (739) to a "formula", which is a formulation or composition of the present invention, as described herein (751), which involves a phase changing material mechanism (741), and a mechanism of stratum corneum recovery (761), it neutralizes insult's effect while fixing the skin barrier (740), (750), (760) by absorption of heat (energy) from the skin (742) which is further released from the formula (762). This mechanism modulates the energy absorbed by the skin and leads to skin regeneration (752) in a mechanism of "bio-mimicry" (753), (754) where, remission from wound progression is achieved (737).

Without being bound to any one particular theory, it is thought that, the mechanism is based on phase-changing materials (PCM), combined with materials aiming to mimic those of the stratum corneum-skin barrier. Being so, it functions as normal skin and can support (766) skin grafts and artificial skin (767).

The composition of the invention itself undergoes a phase change from a liquid crystal to a thin layer crystal upon application on skin and a type of a liquid bandage further promoting the disruption of the pathophysiologic process by absorbing heat from skin (positive enthalpy). During a further phase transition, the heat is released from the formulation or composition (negative enthalpy), the insult is neutralized (740), (750), and (760). With this, there is an "exit" from chronic phase to acute phase and from acute phase (770) to normal skin function.

In another aspect, the present application provides methods for preparing the compositions of the invention.

Figure 1B:
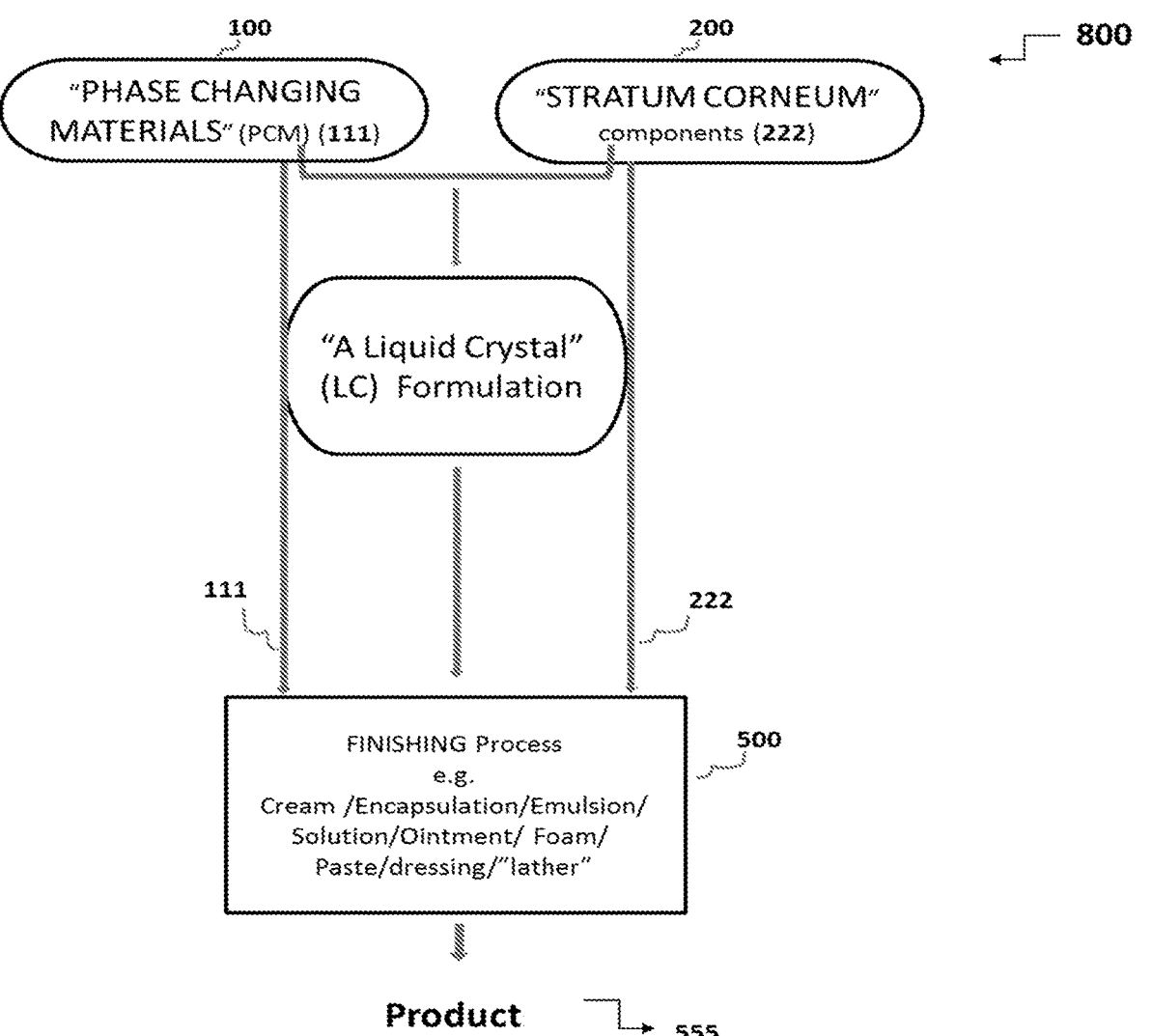

FIG. 1B is a simplified schematic of a flowchart of a summary of steps for preparing a composition for topical application, in accordance with an embodiment of the present invention.

800 is a simplified schematic illustration of parallel or alternative steps to obtain a product composed of phase changing material/s (PCM/s) (100) and stratum corneum (SC) components (200). These are combined to obtain a composition at a liquid crystal (LC) phase, comprising one or more PCM (111, 112) and/or one or more SC component (222, 212), which may be directly subjected to a finishing process (500), to obtain a final product (555).

More specifically, the invention provides methods for preparing compositions for dermal application, comprising combining PCM/s and/or SC components, to form lyotropic Liquid Crystal (LC) mesophases.

A PCM, or a PCM product (a mixture of PCMs) is added to a container/reactor, with a SC component, or a mixture of SC components, optionally with additional lipid/s, such as fatty methyl esters (FME). These are preferably melted and mixed. Melting (30-85° C.), so as to make the material pourable (a "flowable" mixture), with continuous stirring and mixing is better performed in a mixer until complete homogenization is achieved. Mixing can be performed either by hand (i.e., using hand utensils, hand mixers with or without propeller) or with mechanical equipment useful for home, institutional, or industrial food or cosmetic preparation. A dough mixer, often referred to as kneaders is useful. Other applicable mixing equipment includes "Planetary" mixers and Hobart mixers. Extruders, which provide a shearing operation with mixing, can be used (e.g. The Sigma Mixer with extruder). The mixer may be featured with a bowl with Jacketing for heating and cooling.

The mixture of PCM and SC components may then be subjected to neutralization and/or saponification with a base. A "Base" could be an alkaline, an alkaline earth or transition metals or their compounds e.g., oxides, hydroxides, carbonates, sulfates and chlorides, which are used in alkali metal salt production (e.g. NaOH) in DDW, tincture, extract, vegetable milk, animal milk, oil etc. Although not necessary, the saponification may take place in a batch reactor, but occurs only following addition of one or more soluble base/s according to saponification numbers, as known in the art (e.g. squalane SAP NaOH: 0.1340, Lecithin SAP: 0.110-0.140).

In general, alkali metal salts are composed of a metal and acid portion supplied as solutions in solvent or oil. They can be represented by the general formula $(RCOO)xM$ where R is an aliphatic or alicyclic radical and M is a metal with valence x. In the case of neutral salts, x equals the valence of the metal M. Acid salts (the ratio of acid equivalents to metal equivalents is greater than one) contain free acid whereas neutral salts contain no free acid.

Alkali metal salts are soluble, sparingly soluble or insoluble. The selection of metal ion source and fatty acid depends on process type and methods known in the art. Metal salts, in this case preferably fatty acid salts, usually include those of sodium, aluminium, barium, cadmium, calcium, cobalt, copper, iron, lead, lithium, magnesium, manganese, potassium, nickel, zinc and zirconium. Significant application areas for metal salts include lubricants and gel thickeners, emulsifiers, water repellants and fungicides. Suitable alkali metal cations are those of potassium and sodium. Suitable salt counter-ions include alkali metal, alkaline earth metal, ammonium, alkyl or hydroxyalkyl ammonium cations and mixtures thereof. Small amounts of sulfate salts may also be desirably present. These salts may be selected from the group consisting of bisulfite, hydrosulfite, metabisulfite, sulfite and mixtures thereof.

A hydrated salt or saponified material of approx. 60-80% salt with 40-20% $H_2O$, is obtained, preferably 70:30. The 70:30 hydrated salt, is known as the "neat"/"smectic"/ "lamellar" phase in the process of saponification.

This mixtures form a lamellar liquid crystal (LC) in very low concentration of water/solvent accommodating lipids, as in the stratum corneum structure.

The composition thus, according to a specific embodiment, consists of an alkali (e.g. sodium)-FA-salt at lyotropic liquid crystal phase, which depend on its concentration in the solvent.

The solvent may be water, hydrocarbons or their mixtures, an aqueous phase or a non-aqueous phase (10-60%, specifically 20-40%, more specifically 30%), with or without herb/s and/or fruit/s and/or tree/s- and/or flower/s-extract/s, tincture/s, fusion/s such as mint, aloe, chamomile, centella and all others, vegetal and/or animal milk, honey.

The hydrated salt, may be then further mixed, with one or more additives, including; various drug categories as triethanolamine, trolamine/sodium alginate, anti-inflammatory as steroids, Hydrocortisone, anti-histamines, Coal tar, benzoyl peroxide, antimicrobial/fungal e.g. Silver-based components as Silver Sulfadiazine or Bifonazole, Miconazole Nitrate and others. 3,4diand 3, 4', 5tribromosalicylanildes; 4, 4' dichloro3 (trifluoromethyl) carbanilide; 3,4, 4'trichlorocarbanilide and mixtures, sialic and glycolic acid. Analgesics e.g. lidocaine, therapeutic enzymes, conventional preservatives, fragrance and conventional dyes, pigments and thermotropic pigments, alternate/talc and whitening materials, anti-static and skin conditioning, milk extracts e.g. sine adipe lac. Other additives may be; herbal materials, humectants, anti-oxidants and fillers, clay, honey, astringents as Zinc oxide, Zinc glycerolate. Zinc chloride, magnetic particles, minerals, gold particles, sodium, sodium chloride, chelating agents e.g. pentasodium pentetate, pentetic acid. Adjuvants selected from the group consisting of water miscible or water soluble sunscreen agents or UV protectants e.g. benzyl salicylate, antioxidants e.g. pentaerythrifyl tetra-di-t-butyl hydroxyhydrocinnamate, insect repellents e.g. citronellol, chemical repellents, viscosity modifiers, D-Panthenol, hydrolyzed collagen or animal protein and mixtures etc.

Additional PCM/s and/or SC component/s or mixtures thereof may be added at this stage.

The lyotropic liquid crystal phase of the product obtained, for example lamellar phase, is determined by e.g. bipolar microscopy and/or NMR and/or x-ray. Briefly, liquid crystal (LC) mesophases in the product are determined for example in a Polarized Optical Microscope with a microscope (NIKON ECLIPSE E200). For sample preparation, a pin-tip amount of the product is smeared on the microscope glass slide and then quickly covered by the cover slip. The sample is finger pressed to make it as thin as possible. A 40× objective lens and 10 40× eye lens are used with cross polarizers in bright field to detect birefringence. The micrograph is taken under polarizing microscope. For the purpose of production of the lamellar phase liquid crystal composition of the present invention, for example, the concentration of amphiphilic lipid is selected so that lamellar liquid crystals are selectively formed.

In general, a single-phase region of a lamellar liquid crystal often appears when the concentration of amphiphilic lipid is 50% to 85% by mass. Thus, lamellar liquid crystals are preferably produced in such a concentration range. More specifically, the concentration-temperature range that yields a single-phase region of a lamellar liquid crystal depends on the amphiphilic lipid type. Thus, the concentration may be selected based on the "concentration-temperature dependent phase diagram" of the amphiphilic lipid/water system. More precisely, such temperature may be determined in accordance with a conventional technique involving the preparation of a phase diagram.

If needed a "fine tuning" of the liquid crystal phase may be performed by an evaporation/re-hydration "loop". The LC mesophase product is then further subjected to a finishing process.

In some embodiments, the invention provides a method for preparing a composition for dermal application, the method comprising combining PCM/s and/or SC component/s with materials at, or that form, Liquid Crystal (LC) mesophases.

A PCM or a PCM product (a mixture of PCMs), and a SC component or a mixture of SC components, and optionally several additives and/or any additional lipid, may be combined with at least one liquid-crystal forming material (LC-FM). LC-FM and products may be, for example, a polysaccharide (e.g. Xanthan gum), or oleaginous gels, sodium alginate based on alginic acid and others, in a solvent, preferably water of about 50% and 15-35%, respectively. Surfactants that form lamellar liquid crystals directly from the aqueous solution are for example, lecithines, oligoethyleneglycol-alkyl-ethers, monoglycerides and similar. LC-FM that form lamellar liquid crystals may be; alkali fatty acid-salt/s, egg lecithin, soybean lecithin, digalactosyldiacylglycerol, diglucosyldiacylglycerol, maltosyl phytanyl ether, dialkyl dimethyl ammonium chloride, and polyoxyethylene chain added phospholipid, potassium oleate, amphiphilic lipids that form type I micelles or type I hexagonal liquid crystals, and surfactants. Amphiphilic lipids (curvature modifying lipids) are used as curvature regulating substances.

A person skilled in the art can readily determine the optimal amounts of curvature regulating substances to be added based on a phase diagram for a three component system of amphiphilic lipid/curvature regulating substance/ water. For example, such curvature regulating substances are preferably used in amounts of 20% to 85% by mass, and more preferably 50% to 70% by mass, of the total amount of curvature regulating substances and amphiphilic lipids.

Formulation or composition components are initially mixed and milled in a milling mixer (e.g. cooled roller mill machine), and further refined by extrusion for approx. 8 to 15 min. The refined mix is then subjected to hydration by gradual addition of a solvent, e.g. DDW, tincture, extract, vegetable milk, animal milk, oil in a kneading system with constant stirring for approx. 60 min at 60 to 95° C. and then brought to RT or for approx. 24 h at RT. Additional additives, including PCM and/or SC and/or mixtures thereof and/or lipids may be added to the LC-FM Mix.

A liquid crystal product (e.g. FA-salt hydrate) with intercalated additives and SC and PCM with a hydration of approx. 40-90% salt and 10-60% solvent, preferably water-based solvent, should be obtained. According to a specific embodiment, the liquid crystal product contains 70% salt with 30% $H_2O$. A solvent (water, hydrocarbons or their mixtures or non-aqueous solvent), is then added to the mixture and gentle mixing is continued until homogenization. A liquid crystal mixed with some isotropic solution or some gel can be also used in this example of formulation or composition.

The lyotropic liquid crystal (LC) phase of the product, e.g., lamellar and/or hexagonal phase is determined. Mesophases may range from hexagonal, lamellar, cubic, and inverse topology lyotropic phase, and any mixtures or combinations thereof. If needed, a "fine tuning" of the liquid crystal phase may be performed by an evaporation/rehydration "loop". The lyotropic liquid crystal mesophase product is then further subjected to a finishing process.

In accordance with an embodiment of the present invention, the method for preparing a composition for topical application further includes a finishing process with final stages.

Thus, the invention provides a method for producing a lyotropic liquid crystal composition, as detailed above, the method comprising:

(a) hydrolyzation and/or solubilization and/or saponification of at least one PCM and at least one SC component to produce a product (optionally amphiphilic);

(b) hydration of said product (optionally amphiphilic); and optionally (c) addition of at least one additive.

According to a specific embodiment of the invention, the PCM is a fatty acid salt hydrate, or a phospholipid fatty acid salt hydrate.

The liquid crystal compositions obtained according to the method of the invention can exist at the interface of a foam, emulsion or dispersion. That is, they can exist at the interface of a liquid/liquid system (emulsion), a solid/liquid system (dispersion) or a gas/liquid or gas/solid system (foam). The compositions of this invention may be directly poured into dispensers, cans, bags, sashes, bottles, or tubes, or directly elaborated into a cream, an ointment, a paste or any topical "cream base". Then, the compositions may be spread on fabric dressings (e.g. gausses), "Band-Aids" or directly elaborated into emulsions and lotions or encapsulated, and then combined in an emulsion or in a lotion or in a cream, an ointment, a paste and distributed in dispensers to obtain a product composition.

Accordingly, the compositions of the invention can be applied, smeared, or sprayed, with or without a dressing, directly onto a skin barrier disruption to be treated, or on fabric wipes, paper wipes, silicon pads, band aids, or bandages to be applied on the skin barrier disruption.

The term "emulsion" as used herein refers to a liquid crystal based emulsion and/or a liquid crystal-based gel emulsion. In general, emulsions comprise of oil phase, aqueous phase and other components. The emulsion of the composition of the present invention comprises an oil phase that may include PCM/s and SC component/s, as well as oil/s and alkyl polyglycoside emulsifiers, and the aqueous phase may include deionized water and/or water-based solutions and moisturizing agents (e.g. Cetyl alcohol, dimethicone etc.), hydrocarbons or their mixtures. Mixing and homogenization in aqueous phase can be performed for example in F25 Ultraturrax at 13,000 rpm for 3 min.

The composition of the invention is a lyotropic liquid crystal micro-emulsion, which is obtained by lowering water content of the composition to 10-60%.

Encapsulation of the composition may be performed as previously described and detailed by those in the art.

Foaming/Mousse of the composition may be carried out in the conventional manner by the use of a blowing agent or by mechanical foaming. A foam can be formed directly from a pure liquid crystal formulation or composition. A foam can be also formed from a liquid containing a liquid crystal formulation. If a blowing agent is used, it may be any one of the conventional blowing agents, which release a gas such as nitrogen, carbon dioxide. Alternatively, the blowing agent may be one which is decomposed by reacting with another ingredient in the emulsion to liberate a non-coagulating gas as a reaction product.

If mechanical foaming is used, it may be carried out by the use of conventional whipping apparatus, or by pumping the emulsion through foaming heads of the conventional type. A suitable propellant, such as carbon dioxide, propane/butane/isobutene is blend at 40-60 psi or higher, with dimethyl ether or nitrogen, dispensed as a mousse and filled into pressure cans, as known in the art, to obtain a product composition.

The foaming agent used in the practice of the invention may consist of one or more of the following mentioned substances, however, the compositions include liquid crystal materials and/or alkali metal salt, that are known as foaming agents and foam stabilizers themselves. If desired, foaming agent may include, one or more foam stabilizers or boosters, such as methyl cellulose, polyvinyl alcohol, aliphatic alcohols having from 10 to 16 carbon atoms, condensation products of ethylene oxide with fatty alcohols, alkyl aryl polyethoxyethanols, alkali metal salts of alkyl aryl sulfonates, alkali metal salts of sulfonated alkyl aryl polyethoxyethanols, colloidal silica, and alkali metal salts of water soluble polyacrylates.

Foaming agents which may be used in the practice of the invention include, alkyl sulfates of alkali metals in which the alkyl radical has from 12 to 14 carbon atoms, such as sodium lauryl sulfate; alkali metal salts of sulfated condensation products of ethylene oxide with an aliphatic alcohol having from 10 to 18 carbon atoms; alkali metal salts of esters of alpha-sulfo substituted fatty acids having from 10 to 16 carbon atoms; alkali metal salts of palmitic acid or an unsaturated fatty acid having more than 14 carbon atoms such as oleic acid or linoleic acid; alkali metal salts of amphoteric surfactants of the general formula RRNR-"COOH in which R is an alkyl radical having from 10 to 18 carbon atoms, R is hydrogen or an alkyl radical having not more than 12 carbon atoms and R" is a divalent aliphatic hydrocarbon radical having from 1 to carbon atoms; alkali metal salts of esters of sulfo acetic acid with an aliphatic alcohol having from to 18 carbon atoms; alkali metal salts of alkyl isothionates in which the alkyl radical has from 10 to 18 carbon atoms; alkali metal salts of amides of sulfo-substituted fatty acids having from 10 to 16 carbon atoms; tetra alkali metal salts of N-(1,2-dicarboxy ethyl) N-alkyl sulfo-succinamic acids; di alkali metal salts of N-alkyl sulfo-succinamic acids; alkali metal salts of N-methyl taurates of fatty acids having from 10 to 14 carbon atoms; amphoteric surfactants having the general formula HO CHzCOOM in which R is an alkyl radical having from 10 to 18 carbon atoms, R' is H, Na or CH COOM, and M is Na or an organic base; and amphoteric surfactants having the general formula $HO\ C_zEL_zSO_aC$ in which R is an alkyl radical having from 10 to 18 carbon atoms and M is Na or an organic base.

A typical topical "cream base" contains cetyl alcohol, methyl paraben, propylene glycol propylparaben, purified water, sodium lauryl sulfate, and stearyl alcohol and an ointment, mineral oil and white petrolatum.

Thus, a product according to the present invention may be a foam/mousse in a pressure can, a paste, a cream, an ointment, a lotion, a solution, a soap, an emulsion, a dressing, a dressing additive, a liquid bandage, a "roll-on", with or without encapsulated particles. They can also be incorporated in cosmetics (e.g., foundations, eye-makeup, pigmented or non-pigmented lip treatments, e.g., lipsticks, and the like), and in any formulation or composition supporting cure and/or protecting and/or dealing aesthetics of the integumentary system. Suitable products may be in the form of ointments or salves, creams, emulsions, gels, foams, mousses, sprays or medicated dressings or bandages, which must be directly applied on the skin or the affected zone and must be kept into contact with the skin and the integumentary system.

EXAMPLES

Example 1

FIG. 2A is an image of a process performed to obtain dermal burn insults, in accordance with an embodiment of the present invention.

Dermal burn insults are obtained by using a 300 mm brass rod stick previously immersed in boiling water, applied under sterile and monitored conditions for 50 sec on dorsal skin of a 3 month old female pig, according to ethics committee instructions. The pig's skin is exposed to the stick, without adding any pressure to own weight, when it reaches a temperature of 70° C. Each spot is marked and monitored over time, without application (N2) of a formulation (No treatment/Untreated); with application of control-treatment, Silverol (51); and with application of A Composition (D1) in accordance with an embodiment of the present invention. Comparing to the non-burned skin (pink), pale (off-white) spots, characterizing deep-second burns, are formed immediately following a 50 sec of exposure of the skin to the hot stick. This indicates loss of vascularization.

FIG. 2B is a graphical presentation of energy (temperature) measured on dermal burn insults before and after application of a composition according to the invention, and after application of control-silver based treatment. Skin temperatures (° C.), of dermal dorsal burn insults, previously induced using a 300 mm brass stick immersed for 50 sec in boiling water, on a 3 month old pig (female) before ("Control") and following 1 hr, 3 hrs., 24 hrs., and 72 hrs time, without application of a formulation ("No treatment"); with application of control, silver-based treatment, "Silverol"; and with application of "A composition" in accordance with an embodiment of the present invention. The treatment with the Composition of the invention at 1 hr demonstrated a statistically significant modulation of energy on skin, showing a 1-3 degrees decrease when compared to untreated burn spots. The Silver-based known in the art treatment (Silverol) showed results similar to the untreated burn. Representative of two experiments with similar results (n=3). P<0.05.

Example 2

FIG. 3A is an image of dermal burn insults before and after application of a composition according to the invention ("A Formula), and after application of control-silver based treatment ("Silverol"). Dermal dorsal insults were obtained using a 300 mm brass stick immersed for 50 sec in boiling water, on a 3 month old pig (female). The insults were inspected after 15 days' time without application (N2) of a formulation (No treatment); with application of control-treatment, Silverol (S1); and with application of A Formula (D1) in accordance with an embodiment of the present invention. Compared to the untreated burn site (N2), the treatment with the formula showed by day 15 an initiation of vascularization (re-vascularization), initiation of epithelial tissue recovery (re-epithelization) and eschar fall-off. The Silver-based known in the art treatment (Silverol) showed results similar to those of the untreated burns. Representative of two experiments with similar results (n=3).

FIG. 3B is a graphical presentation of dermal burn insults before and after application of a composition according to the invention ("A Formula"), and after application of control-silver based treatment. Dermal dorsal insults were obtained at 70° c. using a 300 mm brass stick immersed for 50 sec in boiling water, on a 3 month old pig (female). The insults were inspected after 15 days' time; without application of a formulation ("No treatment"); with application of control-treatment, "Silverol"; and with application of a composition according to the invention ("A Formula"). Compared to the untreated burn site (No Treatment), the treatment with the composition (A Formula) showed by day 15 a statistically significant initiation of vascularization (re-vascularization), initiation of epithelial tissue recovery (re-epithelization) and eschar fall-off. The Silver-based known in the art treatment (Silverol) showed results similar to those of the untreated burns, with primary necrotic tissue. Representative of two experiments with similar results (n=3). P<0.02.

Example 3

FIG. 4A is an image of dermal burn insults before and after application of a composition of the invention, and after application of control-silver based treatment. Dermal dorsal insults were obtained at 70° c. using a 300 mm brass stick immersed for 50 sec in boiling water, on a 3 month old pigs (female). The insults were inspected after 18 days' time without application (N1, N2 and N3) of a formulation (No treatment); with application of control-treatment, Silverol (S1, S2 and S3); and with application of a composition according to the invention ("A Formula") (D1, D2 and D3). Compared to the untreated burn sites (N1-N3), the treatment with the composition of the invention (D1-D3 and in particular, D2) showed by day 18 an epithelial tissue recovery (re-epithelization) and eschar fall-off. The Silver-based known in the art treatment (Silverol) showed results similar to those of the untreated burns, with primary necrotic tissue. Representative of two experiments with similar results (n=3).

FIG. 4B is an image of a dermal burn insult after application of a composition in accordance with an embodiment of the present invention. Dermal dorsal insults were obtained at 70° c. using a 300 mm brass stick immersed for 50 sec in boiling water, on a 3 month old pigs (female). The insults were inspected after 24 days' time, with application of a composition (D2) in accordance with an embodiment of the present invention. Skin Marker on insult spot and on eschar (right hand side) showed a 70% decrease in wound diameter from 300 to 100 mm.

FIG. 4C is a graphical presentation of diameters measured (mm) from dermal burn insults before and after application of a composition of the invention and after application of control-silver based treatment. Dermal dorsal insults were obtained at 70° c. using a 300 mm brass stick immersed for 50 sec in boiling water, on a 3 month old pigs (female). The insults were inspected after 15, 18 and 24 days' and compared to day 0 time—without application of a formulation ("No treatment"); with application of control-treatment, "Silverol"; and with application of a composition of the invention ("A Formula"). Compared to the untreated ("No Treatment") burn site on days 0, 15, 18 and 24, the treatment with the composition (A Formula), showed a statistically significant decrease on burn-site diameter. The Silver-based known in the art treatment (Silverol) showed results similar to those of the untreated burn, with no decrease in burn site diameter. Representative of two experiments with similar results (n=3). P<0.02.

Example 4

FIG. 5 is a light microscope images (×40) of hematoxylin-eosin (H&E) staining on skin-sections and camera photographs (inserts) from dermal burn insults before and after application of a composition of the invention, and after application of control-silver based treatment. Dermal dorsal insults were obtained at 70° c. using a 300 mm brass stick immersed for 50 sec in boiling water, on a 3 month old pigs (female). The insults were inspected after 24 days' and compared to day 0 time without application of a formulation ("Untreated"); with application of control-treatment, "Silverol"; and with application of "A Formula" in accordance with an embodiment of the present invention. Compared to the untreated ("Untreated") burn site on day 24 and to normal skin (day 0), the treatment with the composition of the invention (A Formula), showed a significant recovery of the epidermis and the dermis. The Silver-based known in the art treatment (Silverol) showed results similar to those of the untreated burn, with no recovery and damaged layers on burn site skin sections. Representative of two experiments with similar results (n=3).

Example 5

FIG. 6A is an image of a dermal insult before application of a composition in accordance with an embodiment of the present invention. A 12 year old boy was exposed to the sun for almost 5 hours with not enough sun protection. Typical sunburn, with characteristic hyperemia and blistering, was clearly observed. Photo was taken 24 hours post sunburn. Remission from sunburn symptoms was only after 6 days.

FIG. 6B is an image of a dermal UV insult after application of a composition in accordance with an embodiment of the present invention. A 12.5 year old boy was exposed to the sun for almost 5 hours with not enough sun protection. A composition of the invention was applied after the UV insult. Symptoms of typical sunburn, with characteristic hyperemia and blistering, were clearly inhibited, as shown in the photo that was taken 48 hours post sunburn. Remission from sunburn symptoms was detected after less than 2 days.

Example 6

FIG. 7A is an image of a dermal thermal (scald from boiling oil) insult, 5 hours' time after the insult and application of a composition in accordance with an embodiment of the present invention. A few drops of boiling oil were accidently splashed on the hand of a 48 y old lady. The composition was applied after 5 h of thermal insult. A burn injury is clearly detected following 5 h (see hyperemic spots).

FIG. 7B is an image of a dermal thermal insult 4 days' time after application of a composition in accordance with an embodiment of the present invention. A few drops of boiling oil were accidently splashed on the hand of a 48 year old lady. A composition was applied after 5 h of thermal insult. At 48 h of treatment, a clear remission in burn injury spots is clearly detected (see almost absence of hyperemic spots).

FIG. 7C is an image of a dermal thermal insult 7 days' time after application of a composition in accordance with an embodiment of the present invention. A few drops of boiling oil were accidently splashed on the hand of a 48 year old lady. The composition was applied after 5 h of thermal insult. At 7 days of treatment, a total remission in burn injury spots is clearly detected (see absence of hyperemic spots) and skin is exempt from scars or any post-wound phenotype.

Example 7

FIG. 8A is an image of a dermal insult (Xerosis) before application of a composition in accordance with an embodiment of the present invention. An 85 year old lady suffered for 3 years from irritated skin, diagnosed with Xerosis. Desquamation with hyperemia is clearly detected before treatment.

FIG. 8B is an image of a dermal insult 2 weeks' time after application of a composition in accordance with an embodiment of the present invention. An 85 year old lady suffered for 3 years from irritated skin, diagnosed with Xerosis. Desquamation with hyperemia is clearly attenuated after 2 weeks of treatment with the composition.

FIG. 8C is an image of a dermal insult 4 weeks' time after application of a composition in accordance with an embodiment of the present invention. An 85 year old lady suffered for 3 years from irritated skin, diagnosed with Xerosis. Desquamation with hyperemia is clearly almost totally disappeared after 4 weeks of treatment with a formulation.

Example 8

FIG. 9 is a graph of relative blistering, hyperemia (redness) and pain of several subjects after treatment with a topical composition in accordance with an embodiment of the present invention. Several formulations in accordance with the present invention had been indirectly shown to reconstitute epidermal skin barrier function following thermal injury. The formulations were used on an ad hoc basis to treat 18 burns or scalds, finding that blistering, hyperemia (increased blood flow and vessel expansion) and pain are greatly reduced, showing that several formulations have the potential to block dermal injury progression upon insult.

Example 9

Table 2 shows relative pain control, sepsis control, wound control and scar control summary of several "known in the art" burn treatments, compared with a topical composition in accordance with an embodiment of the present invention. Several formulations had been indirectly shown to reconstitute epidermal skin barrier function following thermal injury. Formulations according to the invention were used in pre-clinical experiments (2, n=3) and on an ad hoc basis to treat 12 burns or scalds in humans. In has been found that pain, sepsis, wound and scar were greatly reduced, showing that when compared to hydrogels, antibacterial-based creams and analgesics known in the art, several formulations have the potential to block dermal injury progression upon insult.

TABLE 2

| | Pain Control | Sepsis Control | Wound Control | Scar Control |
|---|---|---|---|---|
| First and Superficial Second-Degree Burns | | | | |
| Hydration therapies: Water-retaining gels and gel dressings that reduce thermal response and increase hydration | +++ | + | ---- | --- |
| Antibacterial, antimicrobial therapies | +++ | +++ | --- | --- |
| A Formula | +++ | +++ | +++ | +++ |
| Second and Third-Degree Burns | | | | |
| Resuscitation therapies: Fluid resuscitation (IV hydration) for stabilization, using formulas such as modified Brooke and Parkland | --- | +++ | +++ | --- |
| Antibacterial therapies: Antibiotics | --- | +++ | +++ | --- |
| Wound coverage and grafting therapies | --- | +++ | +++ | --- |
| Skin grafting, cellular or acellular systems | --- | +++ | +++ | ++ |
| A Formula | +++ | +++ | +++ | +++ |

Example 10

Table 3 shows several known in the art burn treatments. Several formulations had been shown to support different stages of wound development following thermal injury.

TABLE 3

| Product | Manufacturer | Description |
|---|---|---|
| Bepanthen | Bayer Healthcare | A family of skincare ointment products, for the treatment of burns and other wounds. |
| Biafine | Valeant | A water-based emulsion for the treatment of 1st and 2nd degree burns and other superficial wounds, as well as burns from radiation therapy. |
| Silverol | TEVA | A topical silver sulfadiazine antibiotic used in partial thickness and full thickness burns to promote healing and prevent infection. |
| Neosporin | J&J Consumer | Prevents infection in minor cuts, scrapes, and burns. Helps to minimize the appearance of scars. |
| Aloe First | Forever Living Products (FLP) | There are many aloe vera based products for treating minor burns. FLP is the largest producer of *aloe vera* products in the world, including the Aloe First spray "for every first aid kit". |

Example 11

A lyotropic liquid crystal composition in accordance with the present invention is prepared according to the following steps:

a. Preparing a Lipid Phase

PCMs and SC components, as specified in Table 4 below, are mixed and melted in a reactor at 50-70° C., specifically 60° C. The obtained liquid lipid phase is cooled to 40° C.

TABLE 4

| Component | Material | % | (g) |
|---|---|---|---|
| PCM | Lanolin/Cholesterol/Cholesterol sulphate | 10.00 | 10.00 |
| PCM/SC | Triglycerides - Olive oil/Avocado oil/Almond oil | 7.00 | 7.00 |

TABLE 4-continued

| Component | Material | % | (g) |
|---|---|---|---|
| PCM/SC | Triglycerides - Palm oil/Sea butter/Sea Buckthorn/Cocoa butter | 7.00 | 7.00 |
| PCM/SC | Triglycerides - Coconut oil/Neem oil/Pomegranate oil | 6.00 | 6.00 |
| PCM/SC | Sterol/Wax esters (Jojoba/bee wax) | 3.50 | 3.50 |
| PCM/SC | FFA - Palmitic, Hexadecanoic | 4.40 | 4.40 |
| PCM/SC | FFA - Oleic, 9-Octadecenoic (9Z-) | 3.96 | 3.96 |
| PCM/SC | FFA - Linoleic, 9,12-Octadecadienoic (9Z,12Z)- | 1.50 | 1.50 |
| PCM/SC | FFA - Stearic | 1.20 | 1.20 |
| PCM/SC | FFA - Myristic, Tetradecanoic | 0.50 | 0.50 |
| PCM/SC | FFA - Palmitoleic, 9-Hexadecenoic | 0.40 | 0.40 |
| PCM/SC | FFA - Arachidic, n-Eicosanoic | 0.04 | 0.04 |
| SC | Phyto-Squalene | 5.00 | 5.00 |
| PCM/SC | n-Alkanes (Paraffin/*Camelina* wax or oil) | 2.50 | 2.50 |
| SC | Lecithin/Ceramides | 13.00 | 13.00 |
| Total | | 66.00 | 66.00 | b. Preparing an Aqueous Phase of a Base

The aqueous solution of the base comprises the materials detailed in Table 5 below. Said solution is prepared in a plastic container by addition of NaOH to the aqueous solvent (i.e., DDW comprising 0.5% aloe extract powder). Zinc oxide is gradually added and the solution is stirred at 40° C.

TABLE 5

| Component | Material | % | (g) |
|---|---|---|---|
| PCM | Sodium Hydroxide | 8.00 | 8.00 |
| | Zinc Oxide | 3.00 | 3.00 |
| | 0.12 gr pure Herbal extract powder (*Aloe*) in 23 gDDW | 23.00 | 23.00 |
| Total | | 34.00 | 34.00 | c. Preparing an Amphiphilic or Saponified Product

The aqueous solution of the base obtained in step (b) above is slowly added to the lipid phase obtained in step (a) above, in a reactor, for neutralization and/or saponification. The mixture is mixed at 40° C. for approx. 40 min., until a homogenized emulation is obtained. Next, a neutralization and/or saponification reaction takes place by stirring the mixture at 90-95° C. for approx. 90 min. to produce an amphiphilic product or a saponified product.

d. Hydration of the Amphiphilic or Saponified Product

DDW, optionally comprising herbal extract or fruit extract (e.g. green tea, chamomile) is added to the additives specified in Table 6 below, to obtain an aqueous solution. Optionally, the following materials are also added to the aqueous solution: 0.01-0.5% dye/pigment, thermochronic pigment, and/or opacifier TiO2; and/or 0.01-2% drug, skin booster, HA sodium salt, Metal silicate, polysaccharide, analgesic, antibiotic, antifungal, minerals, and/or astringent.

TABLE 6

| Component | Material | % | (g) |
|---|---|---|---|
| | DDW (optional w herbal/fruit extract, e.g. green tea, chamomile) | 20.00 | 20.00 |
| SC | Keratin | 9.00 | 9.00 |
| | *Centella asiatica* extract (gotu kola) | 0.30 | 0.30 |
| | Chelate/antioxidant - pentasodium pentetate | 0.10 | 0.10 |
| | Potassium sorbate | 0.10 | 0.10 |
| | Sodium benzoate | 0.50 | 0.50 |
| | Phenoxyethanol | 1.00 | 1.00 |
| | Etheric oil, Pomegranate essential oil | 0.50 | 0.50 |
| PCM | Glycerol, PEG | 1.00 | 1.00 |
| | Vitamin A-Retinoic acid | 0.50 | 0.50 |
| | Vitamin E acetate (tocopheryl acetate) | 0.50 | 0.50 |
| Total | | 33.5 | 33.5 |

The aqueous solution is slowly added to the amphiphilic or saponified product obtained in step (c) above, in a reactor, and is constantly stirred at 60-70° C. for at least one hour. The reaction mixture is brought to pH 5 to 6 by the addition of an acid, such as lactic acid, citric acid, or salicylic acid. A lyotropic liquid crystal composition comprising a fatty acid salt hydrate is obtained.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A homogenic anisotropic lyotropic liquid crystal product with endothermic properties, for topical application directly to skin of a mammal, mimicking a mammalian stratum corneum skin barrier, comprising:

at least 50 wt % of at least one phase changing material (PCM) and at least one stratum corneum (SC) component, and less than 40 wt % hydrant, said lyotropic liquid crystal product comprising a fatty acid, a fatty acid salt hydrate, or a fatty acid salt, wherein the PCM and SC components are selected such that the product is in the form of a homogenic anisotropic lyotropic liquid crystal phase with endothermic properties, mimicking a mammalian stratum corneum skin barrier.

2. The product of claim 1, wherein the product includes at least 40% w/w amphiphilic molecules.

3. The product according to claim 1, wherein the at least one SC component comprises or is selected from the group consisting of a cholesterol, a squalane, a ceramide, a keratinocyte-derived ingredient, a protein, a keratin, and a keratin-derived ingredient.

4. The product according to claim 1, wherein said hydrant is water or an aqueous phase.

5. The product according to claim 1, comprising at least one additive selected from the group consisting of a vitamin, a sunscreen, a di-glyceride, a tri-glyceride, an antibiotic, an antifungal, citric acid, lactic acid, an insect repellent, an analgesic, an active cosmetic ingredient, a polyol, a disinfectant, an astringent, an herbal extract, a fruit extract, a preservative, a pigment, a thermotropic liquid crystal pigment, an oil, an etheric oil, a perfume, a scent, an anesthesia, an abrasive and an emulsifier.

6. The product according to claim 1 which is a soap, a saponification product, a soap-based composition, a skin-protectant fire extinguishing composition, a skin-protectant fire extinguisher-based composition, a sanitary preparation for medical purposes, a preparation for hygienic purposes, or a preparation for destroying fungi or vermin.

7. The product according to claim 1, wherein the product is adapted for a dermal medical procedure or a veterinary dermal procedure.

8. The product of claim 1, wherein said product provides an attenuation of a skin barrier disruption in the mammal.

9. The product of claim 8, wherein said attenuation of skin barrier disruption comprises attenuation or treatment of a skin disorder.

10. The product of claim 8, wherein said attenuation of skin barrier disruption comprises attenuation or treatment of a deep burn or a local wound.

11. The product of claim 8, wherein said attenuation of skin barrier disruption comprises attenuation or treatment of at least one of a dermal damage, a localized damage, a skin energy disruption, a skin allergy, a skin discomfort, a skin hypopigmentation, a skin perturbation, a superficial full-thickness burn, partial deep burn, a blister, a hyperemia, a local pain, a dermal inflammation and a scarring after acute or chronic injury, and an acute or a chronic skin irritation, a skin chafing or dryness.

12. The product of claim 8, wherein said attenuation of skin barrier disruption comprises attenuation of acute or chronic skin irritation that is at least one of a thermal skin damage, an insect bite, an abrasion, a laser or a radioactivity radiation, an exposure to extreme low temperatures, an acne, a wrinkle, a breast-feeding skin damage, a skin abrasion or an irritation after dry or chafed skin.

13. The product of claim 1, comprising, in a concentration of less than 15% w/w, at least one of a stabilizer, an emollient, a wax, an antiseptic, an antifungal, an antibiotic, an analgesic, an anti-inflammatory, an insect repellent, an humectant, an anesthetic, a mineral, an herb, a fruit, a filler, an additive, a skin booster, a fragrance, and a whitening agent.

14. The product of claim 1, comprising at least 60 wt % of at least one PCM and at least one SC component.

15. The product according to claim 1, wherein the at least one PCM comprises a triglyceride, a free fatty acid, a phospholipid, or an n-alkane.

16. The product according to claim 1, comprising up to 20 different PCM and/or up to 20 different SC components.

17. The product of claim 1 wherein the at least one PCM and the at least one SC component further comprise at least one component selected from the group consisting of a saturated or unsaturated fat, a lipid, a fatty acid ester, a glycerol ester, an amphipathic lipid, a homo- and/or hetero-triglyceride, a diglyceride, a monoglyceride, a triacylglycerol, a non-polar lipid, a glycerolphosphate ester, a glycero-phosphatide, a phosphatidic acid, phosphatidyl choline, phosphatidyl ethanolamine, phosphatidyl serine, phosphati-dyl inositol, a phospholipid, a sphingolipid, a plasmalogene, a sterol, a sterol ester, a prenol lipid, a polyprenol, a prenol ester, an alkane, a protein, a liposome, and a hygroscopic material.

18. A method of treating, alleviating and/or attenuating skin barrier disruption in a mammalian subject having a skin barrier disruption, the method comprising topically admin-istering the lyotropic liquid crystal product of claim 1 to the skin area in the vicinity of the skin barrier disruption site in said subject.

19. The method of claim 18, wherein said treating, alleviating and/or attenuating skin barrier disruption com-prises repairing, regenerating or mimicking stratum cor-neum structure and/or function.

20. The method of claim 18, wherein said treating, alleviating and/or attenuating skin barrier disruption com-prises attenuating, and/or inhibiting at least one of a wound following thermal injury, mechanical injury, radiation injury, laser injury, insect bites, abrasion, extreme low temperature injury, acne, wrinkles, skin dryness, and/or chronic skin conditions involving disruption of skin barrier.

21. The method of claim 18, wherein said treating, alleviating and/or attenuating skin barrier disruption com-prises treating, alleviating and/or attenuating wound pro-gression.

\* \* \* \* \*